United States Patent
Fujita

(10) Patent No.: US 8,559,754 B2
(45) Date of Patent: Oct. 15, 2013

(54) METHOD OF REMOVING FOIL SHADOWS OF A SYNCHRONOUS GRID, AND A RADIOGRAPHIC APPARATUS USING THE SAME

(75) Inventor: Akinori Fujita, Osaka (JP)

(73) Assignee: Shimadzu Corporation, Kyoto (JP)

( * ) Notice: Subject to any disclaimer, the term of this patent is extended or adjusted under 35 U.S.C. 154(b) by 144 days.

(21) Appl. No.: 13/321,624

(22) PCT Filed: May 12, 2010

(86) PCT No.: PCT/JP2010/003221
§ 371 (c)(1),
(2), (4) Date: Nov. 21, 2011

(87) PCT Pub. No.: WO2010/134295
PCT Pub. Date: Nov. 25, 2010

(65) Prior Publication Data
US 2012/0063699 A1 Mar. 15, 2012

(30) Foreign Application Priority Data

May 22, 2009 (JP) ................................. 2009-124466

(51) Int. Cl.
*G06K 9/40* (2006.01)
(52) U.S. Cl.
USPC ........... 382/275; 382/128; 382/131; 382/274; 128/922

(58) Field of Classification Search
USPC .................... 382/128, 130, 131, 132; 128/128
See application file for complete search history.

(56) References Cited

U.S. PATENT DOCUMENTS

| | | | |
|---|---|---|---|
| 6,501,829 B2 | 12/2002 | Matsumoto et al. | |
| 6,557,558 B1 * | 5/2003 | Tajima et al. | 128/897 |
| 7,005,854 B2 * | 2/2006 | Mitchell et al. | 324/309 |
| 7,239,908 B1 * | 7/2007 | Alexander et al. | 600/427 |
| 7,496,619 B2 * | 2/2009 | Aldroubi et al. | 708/446 |
| 7,590,264 B2 * | 9/2009 | Mattes et al. | 382/107 |

FOREIGN PATENT DOCUMENTS

| | | | |
|---|---|---|---|
| JP | 2000-83951 A | 3/2000 | |
| JP | 2002-257939 A | 9/2002 | |

* cited by examiner

*Primary Examiner* — Yosef Kassa
(74) *Attorney, Agent, or Firm* — Cheng Law Group, PLLC

(57) ABSTRACT

Grid foil shadows of a synchronous grid are removable by obtaining an approximate fluoroscopic image by extracting detection signals of pixels not influenced by the grid foil shadows from a fluoroscopic image and carrying out an interpolation process thereon, obtaining a grid foil shadow image by determining a difference between the fluoroscopic image and the approximate fluoroscopic image, obtaining a foil shadow standard image by averaging the grid foil shadow image in a longitudinal direction of the grid foil shadows, and removing the grid foil shadows by determining a difference between the fluoroscopic image and the foil shadow standard image.

12 Claims, 18 Drawing Sheets

| $P_{4(n-1)+1}$ | $P_{4n+1}$ | $P_{4(n+1)+1}$ | $P_{4(n+2)+1}$ | $P_{4(n+3)+1}$ | $P_{4(n+4)+1}$ | $P_{4(n+5)+1}$ |
|---|---|---|---|---|---|---|
| $P_{4(n-1)+2}$ | $P_{4n+2}$ | $P_{4(n+1)+2}$ | $P_{4(n+2)+2}$ | $P_{4(n+3)+2}$ | $P_{4(n+4)+2}$ | $P_{4(n+5)+2}$ |
| $P_{4(n-1)+3}$ | $P_{4n+3}$ | $P_{4(n+1)+3}$ | $P_{4(n+2)+3}$ | $P_{4(n+3)+3}$ | $P_{4(n+4)+3}$ | $P_{4(n+5)+3}$ |
| $P_{4(n-1)+4}$ | $P_{4n+4}$ | $P_{4(n+1)+4}$ | $P_{4(n+2)+4}$ | $P_{4(n+3)+4}$ | $P_{4(n+4)+4}$ | $P_{4(n+5)+4}$ |

Fig. 19 (a)

rth row: $P_{r,1}$, $P_{r,2}$, $P_{r,3}$, $P_{r,4}$, $P_{r,5}$, $P_{r,6}$, $P_{r,7}$, $P_{r,8}$, $P_{r,9}$, $P_{r,10}$, $P_{r,11}$, $P_{r,12}$ ...

Fig. 19 (b)

rth row-A: $P_{r,1}$, $P_{r,5}$, $P_{r,9}$, $P_{r,13}$, $P_{r,17}$, $P_{r,21}$, $P_{r,25}$, $P_{r,29}$, $P_{r,33}$, $P_{r,37}$, $P_{r,41}$, $P_{r,45}$ ...

rth row-B: $P_{r,2}$, $P_{r,6}$, $P_{r,10}$, $P_{r,14}$, $P_{r,18}$, $P_{r,22}$, $P_{r,26}$, $P_{r,30}$, $P_{r,34}$, $P_{r,38}$, $P_{r,42}$, $P_{r,46}$ ...

rth row-C: $P_{r,3}$, $P_{r,7}$, $P_{r,11}$, $P_{r,15}$, $P_{r,19}$, $P_{r,23}$, $P_{r,27}$, $P_{r,31}$, $P_{r,35}$, $P_{r,39}$, $P_{r,43}$, $P_{r,47}$ ...

rth row-D: $P_{r,4}$, $P_{r,8}$, $P_{r,12}$, $P_{r,16}$, $P_{r,20}$, $P_{r,24}$, $P_{r,28}$, $P_{r,32}$, $P_{r,36}$, $P_{r,40}$, $P_{r,44}$, $P_{r,48}$ ...

Fig. 19 (c)

PRIOR ART

METHOD OF REMOVING FOIL SHADOWS OF A SYNCHRONOUS GRID, AND A RADIOGRAPHIC APPARATUS USING THE SAME

TECHNICAL FIELD

This invention relates to a method of removing foil shadows of a synchronous grid which removes scattered radiation of a radiographic apparatus, and a radiographic apparatus using the same, and more particularly relates to a method of removing foil shadows of a synchronous grid by image processing, and a radiographic apparatus using the same.

BACKGROUND ART

Conventionally, an X-ray apparatus includes a grid for reducing image quality degradation due to scattered X-rays. However, when the grid is used, a fine longitudinal pattern due to grid foil shadows is superimposed on radiographic images.

An FPD (Flat Panel Detector) has been used widely as an X-ray detector in recent years. The FPD brings about improvements in the spatial resolution and X-ray sensitivity of radiographic images, and its use is increasing at a rapid rate. However, the greater improvements made in spatial resolution and X-ray sensitivity make the clearer grid foil shadows, which are obstructive to interpretation of radiographic images. In order to remove these grid foil shadows, Patent Document 1 discloses a removing method based on image processing using frequency conversion.

On the other hand, Patent Document 2 discloses a synchronous grid for an FPD. As shown in FIG. 23, a synchronous grid 43 includes grid foil strips 43a arranged as inclined such that each has flat surfaces aligned to a straight line 42 extending between a focus F of an X-ray source 41 and an X-ray detecting plane of an FPD 44. That is, the grid foil strips 43a are inclined to align with direct X-rays.

As shown in FIG. 24, the synchronous grid 43 has the grid foil strips 43a arranged so that grid foil shadows may fall on middles of detecting pixels 47 of the FPD 44. In this way, the positions of the grid foil strips 43a and detection pixels 47 are arranged synchronously. Since scattered X-rays 45 are absorbable by these grid foil strips 43a, noise due to the scattered X-rays 45 can be removed. As distinct from the conventional type grid, the synchronous grid 43 uses no spacers such as of graphite between the grid foil strips 43a. Therefore, direct X-rays 46 are not absorbed, whereby the efficiency of detecting the direct X-rays 46 can be increased.

The grid foil strips of the synchronous grid have the same grid ratio as the grid foil strips of the conventional asynchronous grid, although the intervals between the grid foil strips are different. The synchronous grid has intervals Gp between the grid foil strips, which are longer than those of the asynchronous grid. However, the height A of the grid foil strips along the direction of incidence of direct X-rays is higher in the synchronous grid than in the asynchronous grid. With such construction, grid ratio A/Gp of the synchronous grid can be set equal to the grid ratio of the asynchronous grid. Thus, even if the intervals between the grid foil strips Gp in the synchronous grid are longer than in the conventional grid, by making the height A of the grid foil strips higher, performance in removing noise due to the scattered X-rays 45 can be made the same.

Patent Document 1

Unexamined Patent Publication No. 2000-83951

Patent Document 2

Unexamined Patent Publication No. 2002-257939

DISCLOSURE OF THE INVENTION

Problem to be Solved by the Invention

However, for reasons of manufacture of the grid foil strips and construction for aligning the grid foil strips, the synchronous grid has a certain distortion of the linear grid foil strips and a minute shift in their positions of arrangement. Further, since the height A of the grid foil strips in the synchronous grid is higher than that in the asynchronous grid, the foil shadows of the synchronous grid are susceptible to influences of the distortion of the grid foil strips. Distortion occurs also with the grid foil shadows, which is caused by the distortion and shifting of the grid foil strips. As a result, variations in measurements of the foil shadows will occur to different lines of the grid foil shadows, and density variations will occur to the grid foil shadows. Even if frequency conversion is used for removing the grid foil shadows, the grid foil shadows in a longitudinal pattern cannot fully be removed. Artifacts will also appear due to grid foil shadows failing to be removed.

In a C-arm type X-ray apparatus, an X-ray tube and an FPD of great weight are mounted at opposite ends of a C-arm. Thus, minute bending of the C-arm will occur with movement such as rotation of the C-arm, thereby slightly moving (about 2 mm at most) the position of an X-ray tube focus relative to the FPD. Since the grid foil shadows on the FPD also move with the movement of the X-ray tube focus, the grid foil shadows cannot fully be removed.

This invention has been made having regard to the state of the art noted above, and its object is to provide a method of removing foil shadows of a synchronous grid and an apparatus for removing foil shadows of a synchronous grid, which can remove noise due to distortion of grid foil strips of the synchronous grid.

Means for Solving the Problem

To fulfill the above object, this invention provides the following construction.

A first invention provides a grid foil shadow removing method for a radiographic apparatus having a synchronous grid with grid foil strips arranged at regular intervals so that grid foil shadows fall on middles of pixels which detect radiation, the grid foil shadow removing method comprising an approximate fluoroscopic image calculating step for obtaining an approximate fluoroscopic image by extracting detection signal values of pixels free from influences of the grid foil shadows from a fluoroscopic image and carrying out an interpolation process thereon; a grid foil shadow image calculating step for obtaining a grid foil shadow image by determining a difference between the fluoroscopic image and the approximate fluoroscopic image; a foil shadow standard image calculating step for obtaining a foil shadow standard image by averaging the grid foil shadow image in a longitudinal direction of the grid foil shadows; and a foil shadow removing step for removing the grid foil shadows from the fluoroscopic image based on the foil shadow standard image.

According to the above construction, in the grid foil shadow removing method for a radiographic apparatus having a synchronous grid with grid foil strips arranged at regular intervals so that grid foil shadows fall on middles of pixels which detect radiation, the approximate fluoroscopic image calculating step obtains an approximate fluoroscopic image by extracting detection signal values of pixels free from influences of the grid foil shadows from a fluoroscopic image. Next, the grid foil shadow image calculating step obtains a grid foil shadow image by determining a difference between the fluoroscopic image and the approximate fluoroscopic image. Further, the foil shadow standard image calculating step obtains a foil shadow standard image by averaging the grid foil shadow image in a longitudinal direction of the grid foil shadows. Then, the foil shadow removing step removes the grid foil shadows from the fluoroscopic image based on the foil shadow standard image.

Since the grid foil strips are pulled and held in the direction of the foil strips, relatively small variations occur to the grid foil shadows in the longitudinal direction of the grid foil strips. On the other hand, each grid foil strip has errors due to shape or twisting, and minute errors due to the arranging direction and position. Even if nonuniformity exists in the size of the grid foil shadow for different grid foil strips, the grid foil shadows are averaged in the longitudinal direction of the grid foil shadows, and the grid foil shadows are removed from the fluoroscopic image based on the averaged foil shadow standard image. The averaging can remove amplifier noise, quantum noise and so on which mix at random into each pixel. It is also possible to remove interpolation errors included when calculating the approximate fluoroscopic image. Since no spacers are inserted between the grid foil strips as noted hereinbefore, also with the synchronous grid for which it is particularly difficult to arrange the grid foil strips accurately, the grid foil shadows can be removed without an appearance of artifacts.

It is preferred that the foil shadow removing step removes the grid foil shadows from the fluoroscopic image by a difference between the fluoroscopic image and the foil shadow standard image. The grid foil shadows can be removed simply from the fluoroscopic image by subtracting the foil shadow standard image from the fluoroscopic image.

It is preferred that a smoothing step is provided for preparing divided row data by extracting, on a row-by-row basis, respective numbers of pixels within the regular intervals at which the grid foil strips are arranged, from the foil shadow standard image averaged in the foil shadow standard image calculating step, and smoothing the row data and replacing the original foil shadow standard image therewith; wherein the foil shadow removing step removes the grid foil shadows from the fluoroscopic image by a difference between the fluoroscopic image and the foil shadow standard image smoothed.

According to the above construction, the smoothing step is provided for preparing divided row data by extracting, on a row-by-row basis, respective numbers of pixels within the regular intervals at which the grid foil strips are arranged, from the foil shadow standard image averaged in the foil shadow standard image calculating step, and smoothing the row data and replacing the original foil shadow standard image therewith. It is therefore possible to smooth the foil shadow standard image having been unable to be smoothed in the row direction, for each of the row data divided by the number of pixels arranged between the grid foil strips. This can further remove amplifier noise and quantum noise. The foil shadow removing step determines the difference between the fluoroscopic image and the foil shadow standard image smoothed, and removes the grid foil shadows from the fluoroscopic image.

The foil shadow removing step may include an error component image calculating step for obtaining an error component image from a difference between the grid foil shadow image and the foil shadow standard image; a foil shadow distortion removed image calculating step for obtaining a foil shadow distortion removed image by determining a difference between the fluoroscopic image and the error component image; and a frequency conversion processing step for carrying out a frequency conversion process on the foil shadow distortion removed image to remove the grid foil shadows.

According to the above construction, the error component image calculating step obtains an error component image from a difference between the grid foil shadow image and the grid foil shadow standard image. The foil shadow distortion removed image calculating step obtains a foil shadow distortion removed image by determining a difference between the fluoroscopic image and the error component image. The frequency conversion processing step carries out a frequency conversion process on the foil shadow distortion removed image to remove the grid foil shadows. Since error components of the respective grid foil strips are removed by removing from the fluoroscopic image the error component image which is a difference between the averaged foil shadow standard image and the foil shadow image, the remaining foil shadows can be removed by frequency conversion. Also with the synchronous grid for which it is difficult to arrange the grid foil strips accurately, a frequency conversion process can be carried out to remove the grid foil shadows.

A smoothing step may be provided for preparing row data by extracting and dividing, on a row-by-row basis, respective numbers of pixels within the regular intervals at which the grid foil strips are arranged, from the foil shadow standard image averaged in the foil shadow standard image calculating step, and smoothing the row data and replacing the original foil shadow standard image therewith; wherein the error component image calculating step obtains the error component image by determining a difference between the grid foil shadow image and the foil shadow standard image smoothed.

According to the above construction, the smoothing step is provided for preparing row data by extracting and dividing, on a row-by-row basis, respective numbers of pixels within the regular intervals at which the grid foil strips are arranged, from the foil shadow standard image averaged in the foil shadow standard image calculating step, and smoothing the row data and replacing the original foil shadow standard image therewith. It is therefore possible to smooth the foil shadow standard image having been unable to be smoothed in the row direction, for each of the row data divided by the number of pixels arranged between the grid foil strips. This can further remove amplifier noise and quantum noise. The error component image calculating step determines the difference between the grid foil shadow image and the foil shadow standard image smoothed, and removes the error component image.

It is preferred that an image processing mode selecting step is provided for selecting, based on an amount of an SID and an amount of movement of a C-arm inputted and set, one of a normal correction mode for not correcting movement of the foil shadows between the pixels, and a special correction mode for correcting movement of the foil shadows between the pixels; wherein, when the normal correction mode is selected in the image processing mode selecting step, the approximate fluoroscopic image calculating step extracts the detection signal values of all pixels other than the pixels arranged beforehand to have the grid foil shadows falling thereon, and carries out an interpolation process thereon; and when the special correction mode is selected in the image processing mode selecting step, the approximate fluoroscopic image calculating step extracts the detection signals of pixels located in middles between the grid foil strips and free from the foil shadows even if the foil shadows move, and carries out an interpolation process thereon.

According to the above construction, the image processing mode selecting step, based on an amount of the SID and an amount of movement of the C-arm inputted and set, selects the normal selection mode when the foil shadows do not move across the pixels, and the special correction mode for correcting movement of the foil shadows between the pixels when the foil shadows move across the pixels. When the normal correction mode is selected, the approximate fluoroscopic image calculating step regards all the pixels other than the pixels arranged beforehand to have the grid foil shadows falling thereon as pixels not influenced by the grid foil shadows, extracts the detection signals of these pixels, and carries out an interpolation process thereon. On the other hand, when the special correction mode is selected, the pixels located in the middle between the grid foil shadows and not having the foil shadows even if the foil shadows move are regarded as pixels not influenced by the grid foil shadows, the detection signals of these pixels are extracted, and an interpolation process is carried out thereon. Consequently, when the foil shadows do not move across the pixels, and also when they do, an interpolation process can be carried out appropriately to calculate the approximate fluoroscopic image.

A second invention provides a radiographic apparatus comprising a radiation emitting device for emitting radiation to a patient; a radiation detecting device having pixels arranged in a two-dimensional array for detecting the radiation transmitted through the patient; a synchronous grid arranged at regular intervals so that grid foil shadows fall on middles of the pixels; an approximate fluoroscopic image calculating unit for calculating an approximate fluoroscopic image by extracting a pixel set free from influences of the grid foil shadows from a fluoroscopic image transmitted through the patient and detected and carrying out an interpolation process thereon; a grid foil shadow image calculating unit for obtaining a grid foil shadow image by determining a difference between the fluoroscopic image and the approximate fluoroscopic image; a foil shadow standard image calculating unit for obtaining a grid foil shadow standard image by averaging the grid foil shadow image in a longitudinal direction of the grid foil shadows; and a foil shadow removed image calculating unit for obtaining a foil shadow removed image by removing the grid foil shadows from the fluoroscopic image based on the grid foil shadow standard image.

According to the above construction, in the radiographic apparatus, the radiation emitting device emits radiation to a patient, the radiation detecting device having pixels arranged in a two-dimensional array for detecting the radiation detects the radiation transmitted through the patient, and the synchronous grid is arranged at regular intervals so that grid foil shadows fall on middles of the pixels. The approximate fluoroscopic image calculating unit calculates an approximate fluoroscopic image by extracting a pixel set free from influences of the grid foil shadows from a fluoroscopic image transmitted through the patient and detected, and carrying out an interpolation process thereon. The grid foil shadow image calculating unit obtains a grid foil shadow image by determining a difference between the fluoroscopic image and the approximate fluoroscopic image. The foil shadow standard image calculating unit obtains a grid foil shadow standard image by averaging the grid foil shadow image in a longitudinal direction of the grid foil shadows. The foil shadow removed image calculating unit obtains a foil shadow removed image by removing the grid foil shadows from the fluoroscopic image based on the grid foil shadow standard image.

Thus, even if the grid foil shadows are not uniform, the grid foil shadows are averaged in the longitudinal direction of the grid foil shadows, and the grid foil shadows are removed from the fluoroscopic image based on the averaged foil shadow standard image. Even if nonuniformity exists in the size of the grid foil shadow for different grid foil strips, the grid foil shadows are averaged in the longitudinal direction of the grid foil shadows, and the grid foil shadows are removed from the fluoroscopic image based on the averaged foil shadow standard image. The averaging can remove amplifier noise, quantum noise and so on which mix at random into each pixel. It is also possible to remove interpolation errors included when calculating the approximate fluoroscopic image. Also with the synchronous grid for which it is difficult to arrange the grid foil strips accurately, the grid foil shadows can be removed without an appearance of artifacts.

It is preferred that the foil shadow removed image calculating unit obtains the foil shadow removed image by a difference between the fluoroscopic image and the grid foil shadow standard image. According to this construction, the foil shadow removed image can be obtained simply by subtracting the foil shadow standard image from the fluoroscopic image.

The foil shadow removed image calculating unit may include an error component image calculating unit for obtaining an error component image by determining a difference between the grid foil shadow image and the grid foil shadow standard image; a foil shadow distortion removed image calculating unit for obtaining a foil shadow distortion removed image by determining a difference between the fluoroscopic image and the error component image; and a frequency conversion processing unit for carrying out a frequency conversion process on the foil shadow distortion removed image to remove the grid foil shadows.

The error component image calculating unit obtains an error component image by determining a difference between the grid foil shadow image and the grid foil shadow standard image. The foil shadow distortion removed image calculating unit obtains a foil shadow distortion removed image by determining a difference between the fluoroscopic image and the error component image. The frequency conversion processing unit carries out a frequency conversion process on the foil shadow distortion removed image to remove the grid foil shadows. Thus, even if the grid foil shadows are not uniform, the grid foil shadows are averaged in the longitudinal direction of the grid foil shadows, and the error component image which is a difference between the averaged foil shadow standard image and the foil shadow image is removed from the fluoroscopic image, thereby to obtain a fluoroscopic image having uniform grid foil images. The remaining grid foil shadows can be removed by carrying out a frequency conversion process on this fluoroscopic image. Also with the synchronous grid for which it is difficult to form the shape and arrangement of the respective grid foil strips uniformly, the frequency conversion process can be carried out to remove the grid foil shadows.

It is preferred that an input unit is provided for inputting and setting an amount of an SID and an amount of movement of a C-arm; and an correction mode selecting unit for selecting, based on the amount of the SID and the amount of movement of the C-arm inputted and set, a correction mode from a normal correction mode and a special correction mode; wherein, the approximate fluoroscopic image calculating unit, when the normal correction mode is selected as the correction mode, extracts the detection signal values of all pixels other than the pixels arranged beforehand to have the grid foil shadows falling thereon and carries out an interpolation process thereon, and when the special correction mode is selected as the correction mode, extracts the detection signal values of pixels located in middles between the grid foil strips which are free from the foil shadows even if the foil shadows move and carries out an interpolation process thereon.

According to the above construction, an amount of an SID and an amount of movement of a C-arm are inputted and set to the input unit. The correction mode selecting unit, based on the amount of the SID and the amount of movement of the C-arm inputted and set, selects a correction mode from a normal correction mode and a special correction mode. When the normal correction mode is selected as the correction mode, the approximate fluoroscopic image calculating unit extracts the detection signal values of all pixels other than the pixels arranged beforehand to have the grid foil shadows falling thereon, and carries out an interpolation process thereon. When the special correction mode is selected as the correction mode, it extracts the detection signal values of pixels located in middles between the grid foil strips which are free from the foil shadows even if the foil shadows move, and carries out an interpolation process thereon. Consequently, when the foil shadows do not move across the pixels, and also when they do, an interpolation process can be carried out appropriately to calculate the approximate fluoroscopic image.

It is preferred that a smoothing unit is provided for preparing row data by extracting and dividing, on a row-by-row basis, respective numbers of pixels within the regular intervals at which the grid foil strips are arranged, from the foil shadow standard image calculated by the foil shadow standard image calculating unit, and smoothing the row data and replacing the original foil shadow standard image therewith.

According to the above construction, the smoothing unit prepares divided row data by extracting, on a row-by-row basis, respective numbers of pixels within the regular intervals at which the grid foil strips are arranged, from the foil shadow standard image calculated by the foil shadow standard image calculating unit, and smoothes the row data and replaces the original foil shadow standard image therewith. Consequently, the row data with relatively large variations can be divided into a plurality of smooth row data. As a result, it is possible to smooth the foil shadow standard image having been unable to be smoothed in the row direction, for each of the row data divided by the number of pixels within the regular intervals at which the grid foil strips are arranged. Thus, the foil shadow standard image further inhibiting amplifier noise and quantum noise can be calculated by correcting variations in the respective grid foil shadows.

It is preferred that the synchronous grid and the radiation detector are arranged beforehand so that the grid foil shadows fall on every four pixels. According to this construction, the synchronous grid and the radiation detector are arranged beforehand so that the grid foil shadows fall on every four pixels. Consequently, even if the foil shadows move, the movement of the foil shadows is contained within the adjoining pixels at opposite sides of the pixels arranged beforehand to have the grid foil strips projected thereon. It is therefore possible to provide pixels which certainly have no grid foil shadows falling thereon.

Effects of the Invention

With the method of removing foil shadows of a synchronous grid and the apparatus for removing foil shadows of a synchronous grid according to this invention, a method of removing foil shadows of a synchronous grid and a apparatus for removing foil shadows of a synchronous grid can be provided which can remove noise due to distortion of grid foil strips of the synchronous grid.

BRIEF DESCRIPTION OF THE DRAWINGS

FIGS. 19(*a*), (*b*) and (*c*) are explanatory views showing image processing according to Embodiment 3;

DESCRIPTION OF REFERENCES

Figure 1:
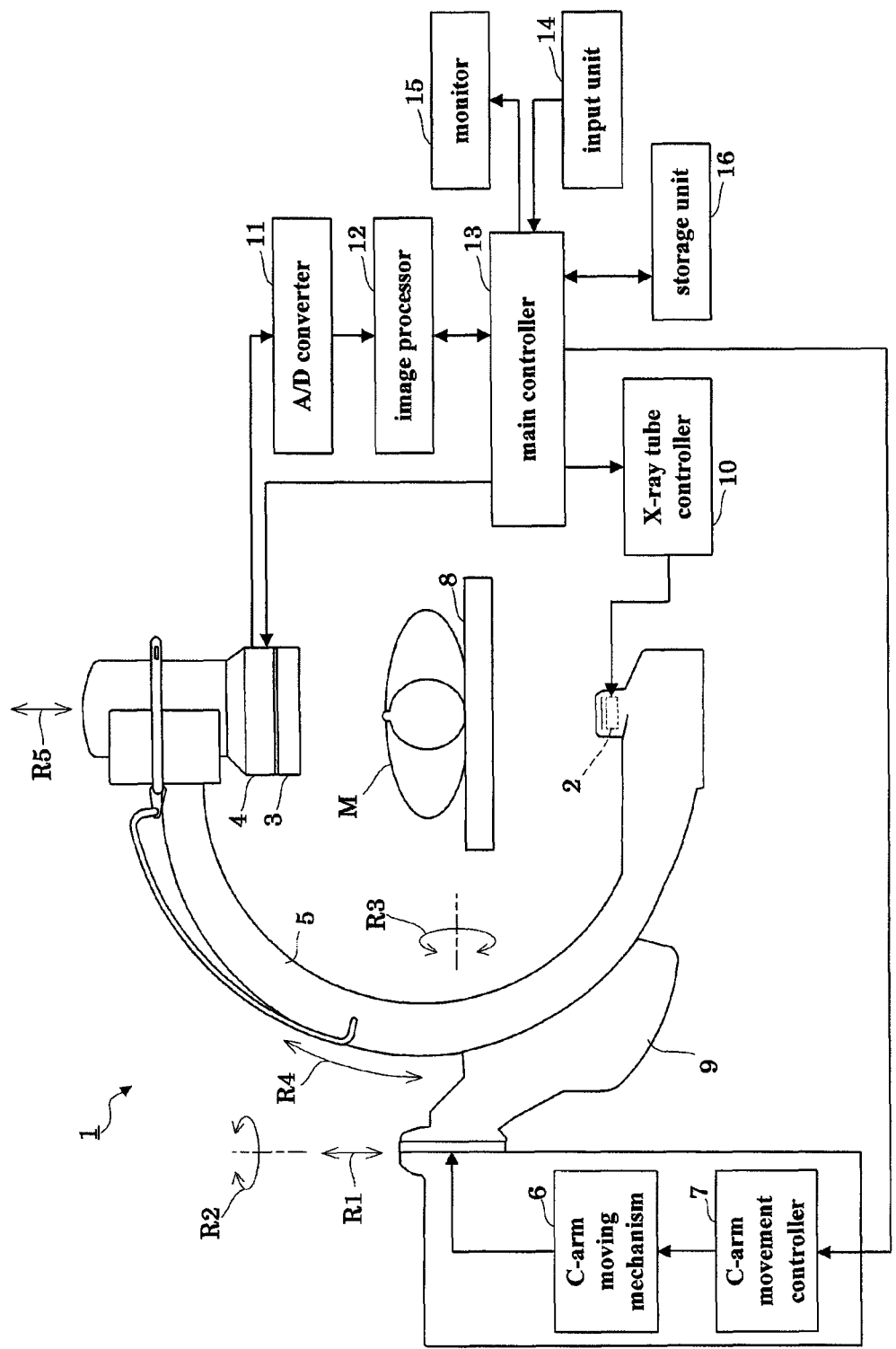
FIG. 1 is an overall view of an X-ray fluoroscopic apparatus according to embodiments.

1 . . . X-ray apparatus
2 . . . X-ray tube

3 ... synchronous grid
4 ... FPD
5 ... C-arm
12 ... image processor
19 ... correction mode selecting unit
20 ... first approximate image calculating unit
21 ... second approximate image calculating unit
22 ... foil shadow image calculating unit
23 ... foil shadow standard image calculating unit
24 ... subtracting unit
33 ... foil shadow removed image calculating unit
34 ... error component image calculating unit
35 ... foil shadow distortion removed image calculating unit
36 ... frequency conversion processing unit
31 ... smoothing unit
37 ... smoothing unit
DU ... X-ray detecting pixels Embodiment 1

Embodiment 1 of this invention will be described hereinafter with reference to the drawings.

Figure 2:
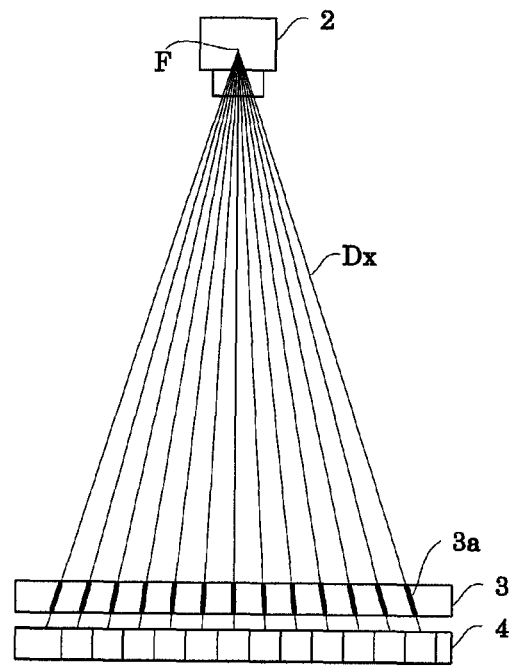
FIG. 2 is a schematic sectional view of a grid of the X-ray fluoroscopic apparatus according to the embodiments.
Figure 3:
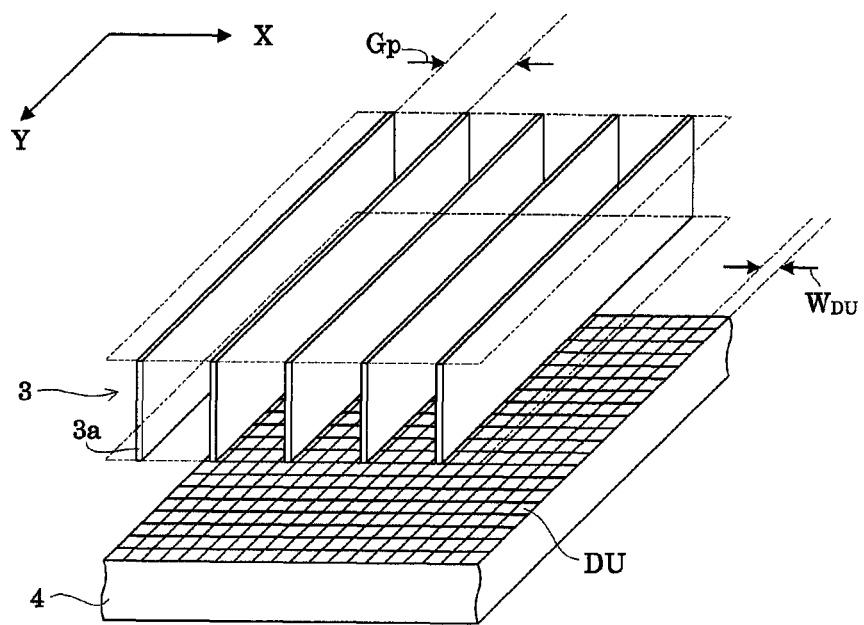
FIG. 3 is a perspective view of grid foil strips of the X-ray fluoroscopic apparatus according to the embodiments.
Figure 4:
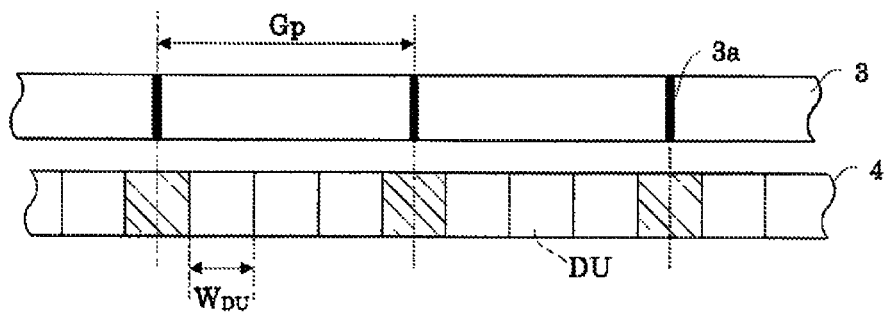
FIG. 4 is a schematic sectional view of the grid and an FPD of the X-ray fluoroscopic apparatus according to the embodiments.

FIG. 1 is an overall view of an X-ray fluoroscopic apparatus. FIG. 2 is a schematic sectional view of a grid. FIG. 3 is a perspective view of grid foil strips. FIG. 4 is a schematic sectional view of the grid and an FPD.

As shown in FIG. 1, an X-ray fluoroscopic apparatus 1 includes an X-ray tube 2 for emitting X-rays to a patient M, a synchronous grid 3 for removing scattered X-rays from transmission X-rays transmitted through the patient M, and a flat panel detector (hereinafter called FPD) 4 for detecting the transmission X-rays from which the scattered X-rays have been removed. The X-ray tube 2 and the synchronous grid 3/FPD 4 are attached to opposite ends of a C-arm 5 to be opposed to each other. This C-arm 5 is moved by a C-arm moving mechanism 6, and an amount of movement of the C-arm moving mechanism 6 is controlled by a C-arm movement controller 7. The X-ray tube 2 corresponds to the radiation emitting device in this invention. The FPD 4 corresponds to the radiation detecting device in this invention.

The C-arm 5 is constructed movable up and down (R1) in vertical directions relative to a top board 8 on which the patient M is placed. An arm support 9 which supports the C-arm 5 is attached to be rotatable (R2) about an axis extending vertically. The C-arm 5 is attached to be rotatable (R3) about a horizontal axis and movable arcuately (R4) relative to the arm support 9. In order to adjust an SID (Source Image Distance) which is a distance between the X-ray tube 2 and the synchronous grid 3/FPD 4, the synchronous grid 3 and FPD 4 are movable in vertical directions (R5) by the C-arm moving mechanism 6.

The X-ray fluoroscopic apparatus 1 further includes an X-ray tube controller 10 for controlling a tube current and tube voltage outputted to the X-ray tube 2, an A/D converter 11 for converting analog X-ray detection signals outputted from the FPD 4 into digital X-ray detection signals, an image processor 12 for carrying out various image processes from the digital X-ray detection signals, a main controller 13 for performing overall control of these components, an input unit 14 for the radiographer to make varied inputs and settings, a monitor 15 for displaying X-ray diagnostic control screens, X-ray transmission images having undergone image processing, and so on, and a storage unit 16 for storing the X-ray transmission images and other radiographic data.

The main controller 13 is constructed of a central processing unit (CPU) and the like. The input unit 14 is constructed of a pointing device represented by a mouse, keyboard, joystick, trackball, touch panel and so on. The radiographer can input settings concerning the SID and amounts of movement of the C-arm by operating the input unit 14. The monitor 15 may be a liquid crystal display or a CRT display, for example. The storage unit 16 may be a hard disk or memory.

As shown in FIGS. 2 and 3, the synchronous grid 3 is disposed to cover an X-ray detecting plane of the FPD 4. The synchronous grid 3 has grid foil strips 3a extending in a longitudinal (Y) direction for absorbing X-rays. The grid foil strips 3a are arranged as inclined such that each has flat surfaces aligned to a straight line extending between a focus F of an X-ray source of the X-ray tube 2 and the X-ray detecting plane of the FPD 4. That is, the grid foil strips 3a are inclined to align with direct transmission X-rays Dx. The synchronous grid 3 has the grid foil strips 3a arranged so that grid foil shadows (hereinafter called simply foil shadows) may fall on middles of X-ray detecting pixels DU of the FPD 4.

As shown in FIGS. 3 and 4, the grid foil strips 3a are arranged at predetermined intervals in a transverse (X) direction, and the arrangement pitch Gp is 400 μm in Embodiment 1. This arrangement pitch Gp is designed as appropriate to synchronize with the width $W_{DU}$ of the X-ray detecting pixels DU of the FPD 4. That is, the grid foil strips 3a are arranged so that the foil shadows thereof may be cast at predetermined pixel intervals on the X-ray detecting pixels DU when in a C-arm standard position at a reference SID. Since the width $W_{DU}$ of the X-ray detecting pixels DU is 100 μm in Embodiment 1, the foil shadows will be cast in a ratio of one to four X-ray detecting pixels DU in the transverse direction.

The grid foil strips 3a are formed from a simple substance such as molybdenum, tungsten, lead or tantalum, or an alloy having one of these as main component. For this metal, it is preferable to select a material having a large atomic number and large X-ray absorption, and its thickness usually is 20-50 μm. The grid foil strips 3a are manufactured by rolling, cutting and so on, but because of being a heavy metal or an alloy of heavy metals as noted above, it is very difficult to secure strictly shape uniformity such as in the thickness and width of the grid foil strips 3a. This shape nonuniformity of the grid foil strips 3a becomes a cause of variations in detection values of the foil shadows.

The FPD 4 has, for example, 2000×2000 X-ray detecting pixels DU arranged in a two-dimensional array for converting X-rays into charge signals. The X-ray detecting pixels DU consist of X-ray detecting elements which generate charge signals when irradiated with X-rays.

The SID is a perpendicular distance between the focus of the X-ray source in the X-ray tube 2 and the FPD 4. When the SID is short, an enlarged fluoroscopic image of the patient M can be obtained. When the SID is long, a wide-angle fluoroscopic image of the patient M can be obtained. That is, a zoom adjustment of fluoroscopic images can be made by adjusting the SID. In Embodiment 1, the SID at 1000 mm is set as reference SID. The grid foil strips 3a and FPD 4 are positionally adjusted to have the foil shadows falling on the X-ray detecting pixels of the FPD 4 in the ratio of one to four in the transverse direction when in the C-arm standard position at the reference SID. The C-arm standard position is a position in which, as shown in FIG. 1, the C-arm 5 is in a positional relationship set three-dimensionally relative to a bed and top board 8 or an examination room, and to which the C-arm 5 is initialized for every examination. It is a standard position where the C-arm 5 is considered free from bending, in order to carry out a positional adjustment of the synchronous grid 3 and FPD 4 in this position.

Figure 5:
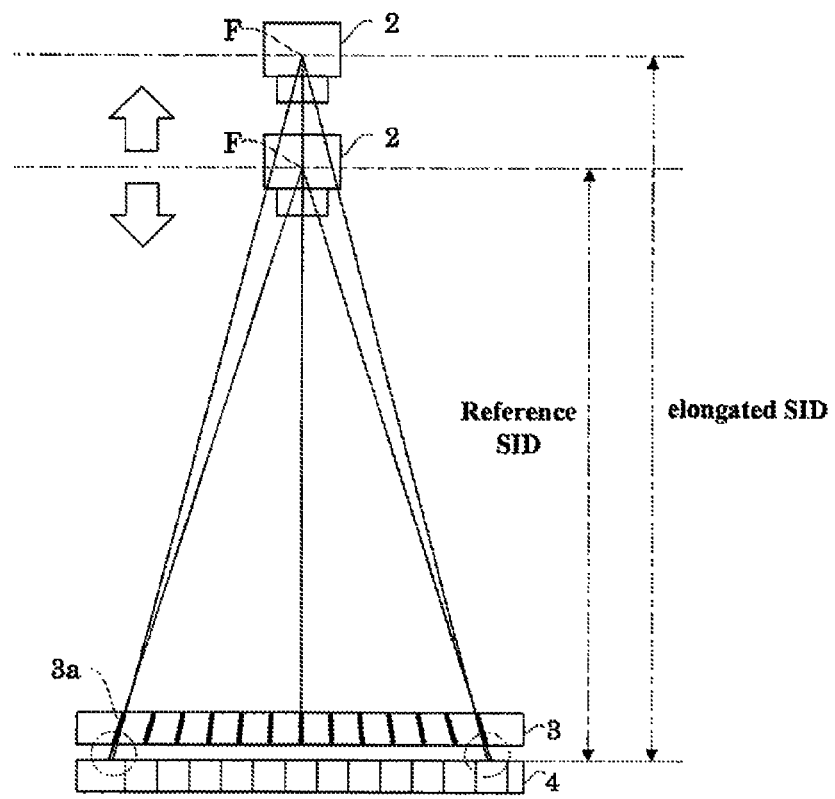
FIG. 5 is an explanatory view of SIDs of the X-ray fluoroscopic apparatus according to the embodiments.

When this SID is changed, the foil shadows on the X-ray detecting plane will move. When the SID is made longer than the reference SID as shown in FIG. 5, for example, although the foil shadows on a middle portion of the FPD 4 are little influenced, the foil shadows closer to side ends of the FPD 4 move inward of the FPD 4. Conversely, when the SID is made shorter than the reference SID, the foil shadows move outward of the FPD 4.

Figure 6:
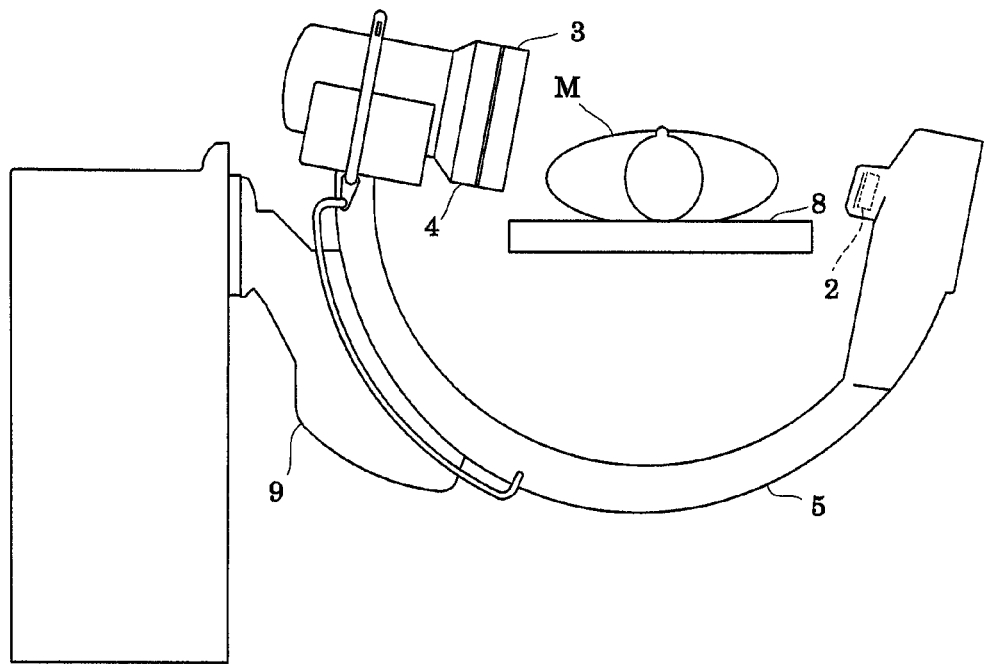
FIG. 6 is a schematic view of the X-ray fluoroscopic apparatus according to the embodiments.
Figure 7:
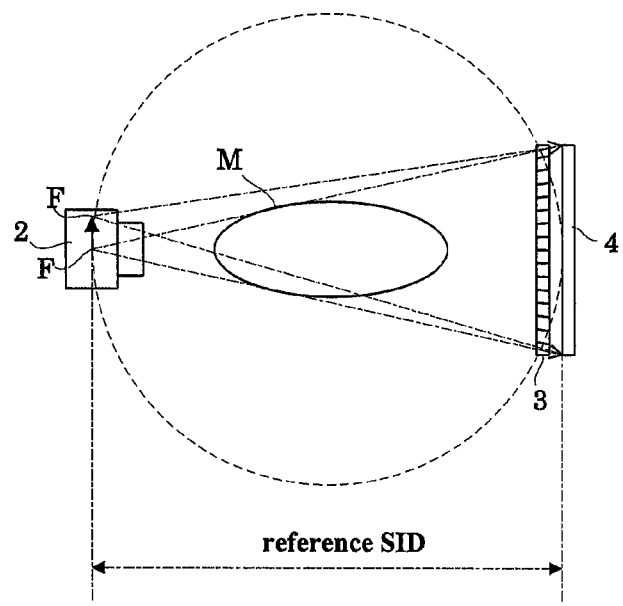
FIG. 7 is an explanatory view illustrating movement of an X-ray focus of the X-ray fluoroscopic apparatus according to the embodiment.
Figure 8:
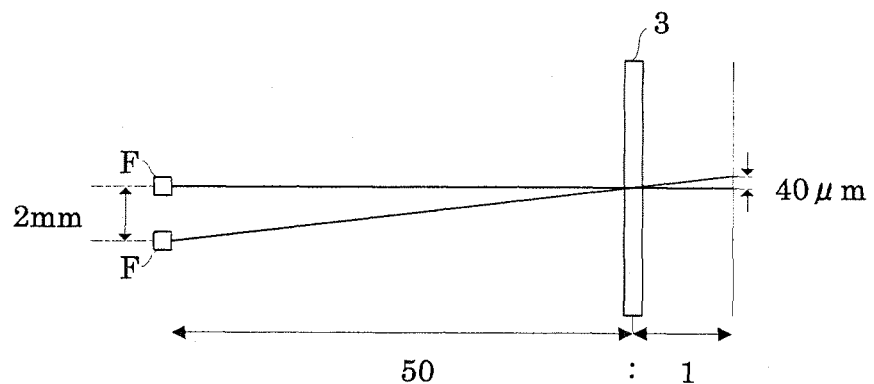
FIG. 8 is an explanatory view illustrating movement of the X-ray focus of the X-ray fluoroscopic apparatus according to the embodiments.

Movement of the foil shadows occurs also when the C-arm 5 is moved, e.g. rotated. When the C-arm 5 is rotated as shown in FIG. 6, bending will inevitably occur to the C-arm 5 due to the rigidity of the C-arm 5. When the X-ray focus in the X-ray tube 2 moves with this bending, the foil shadows will minutely move also at the reference SID. The amount of movement of the X-ray focus due to the bending of the C-arm 5 is about 2 mm at most. As shown in FIG. 7, for example, when X-ray focus F in the X-ray tube 2 moves minutely, the straight lines extending between the X-ray focus F and the detecting plane of the FPD 4 will become misaligned with the inclination angles of the flat surfaces of the grid foil strips 3a. Consequently, the foil shadows will move minutely on the X-ray detecting plane. Regarding the amount of movement of the foil shadows, as shown in FIG. 8, when the SID is 1000 mm and the distance between the synchronous grid 3 and the FPD 4 is 20 mm, the ratio between the distance from the focus F of the X-ray tube 2 to the synchronous grid 3 and the distance from the synchronous grid 3 to the FPD 4 is about 50:1. Consequently, when the X-ray source moves 2 mm, the foil shadows of the grid foil strips 3a will move about 40 µm on the detecting plane of the FPD 4.

Figure 9:
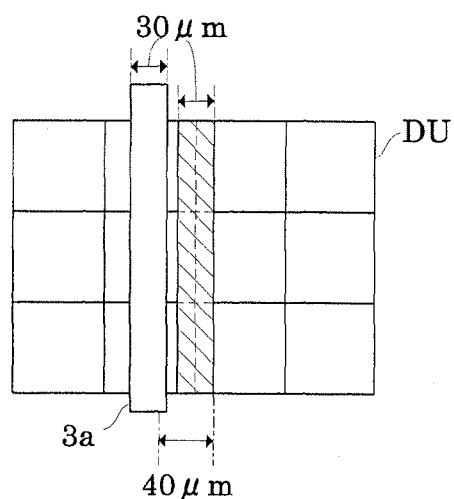
FIG. 9 is an explanatory view illustrating movement of a foil shadow on pixels of the FPD according to the embodiments.

Assume that the thickness of the grid foil strips 3a is 30 µm, and the width of the foil shadows is also 30 µm, when the X-ray tube focus has not moved at the reference SID, since a setting is made such that the foil shadows are located at the middles of the pixels, there is an allowance of 35 µm from the foil shadows to adjoining pixels. However, when foil shadows move 40 µm as described above, as shown in FIG. 9, the foil shadows will protrude into the adjoining pixels from the pixels arranged beforehand to have the foil shadows cast thereon.

Thus, there occur two possibilities, which are a case where the foil shadows remain in the pixels synchronized beforehand to fall thereon, and a case where the foil shadows straddle the pixels or completely move into pixels adjoining the synchronized pixels. So, the image processor 5 carries out a foil shadow correction appropriate to each case.

Figure 10:
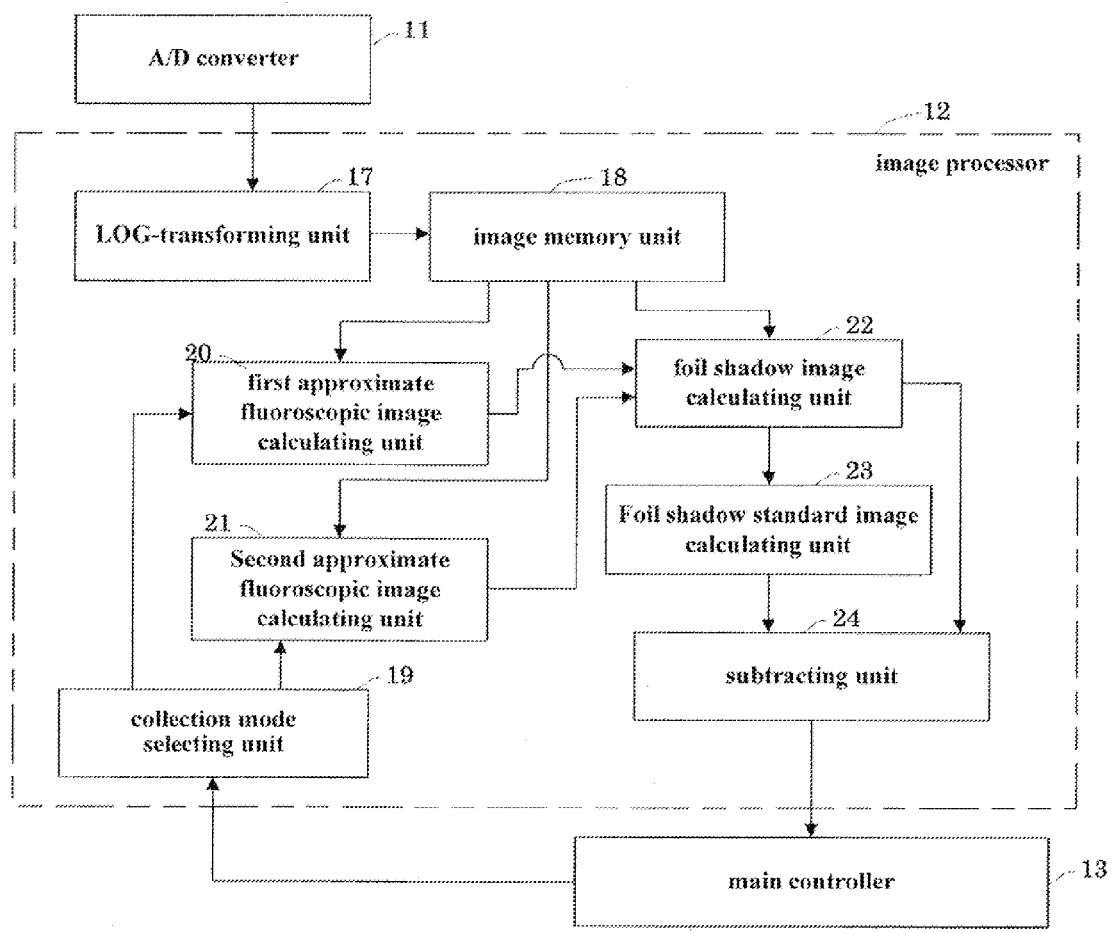
FIG. 10 is a block diagram showing a construction of an image processor according to Embodiment 1.

Next, reference is made to FIG. 10. FIG. 10 is a block diagram showing the construction of the image processor. The image processor 12 includes a LOG-transforming unit 17 for LOG-transforming the digital X-ray detection signals converted by the A/D converter 11, an image memory unit 18 for storing the LOG-transformed X-ray detection signals corresponding to some images, a correction mode selecting unit 19 for selecting a foil shadow correction mode based on an amount of the SID or an amount of movement of the C-arm 5 set through the input unit 14, a first approximate fluoroscopic image calculating unit 20 and a second approximate fluoroscopic image calculating unit 21 for electing pixel sets not influenced by the foil shadows from an X-ray detection image stored in the image memory unit 18 and calculating an approximate fluoroscopic image of the patient M, a foil shadow image calculating unit 22 for calculating a grid foil shadow image from a difference between the X-ray detection image and approximate fluoroscopic image, a foil shadow standard image calculating unit 23 for calculating a grid foil shadow standard image by averaging the grid foil shadow image, and a subtracting unit 24 for calculating a foil shadow removed X-ray detection image by calculating a difference between the X-ray detection image stored in the image memory unit 18 and the grid foil shadow standard image.

The LOG-transforming unit 17 LOG-transforms the digital X-ray detection signals converted by the A/D converter 11. Consequently, the X-ray detection signals can be calculated by linear sum, which can simplify subsequent arithmetic operations.

The image memory unit 18 stores some X-ray detection images formed of the X-ray detection signals LOG-transformed by the LOG transforming unit 17. The image memory unit 18 functions also as a buffer.

The correction mode selecting unit 19 selects a normal correction mode or a special correction mode as the mode for correcting the foil shadows. This selection is executed based on an amount of the SID and an amount of movement of the C-arm 5 inputted and set to the input unit 14 and sent through the main controller 13. Here, the amount of movement is an amount of movement of the C-arm 5 from the C-arm standard position.

Figure 11:
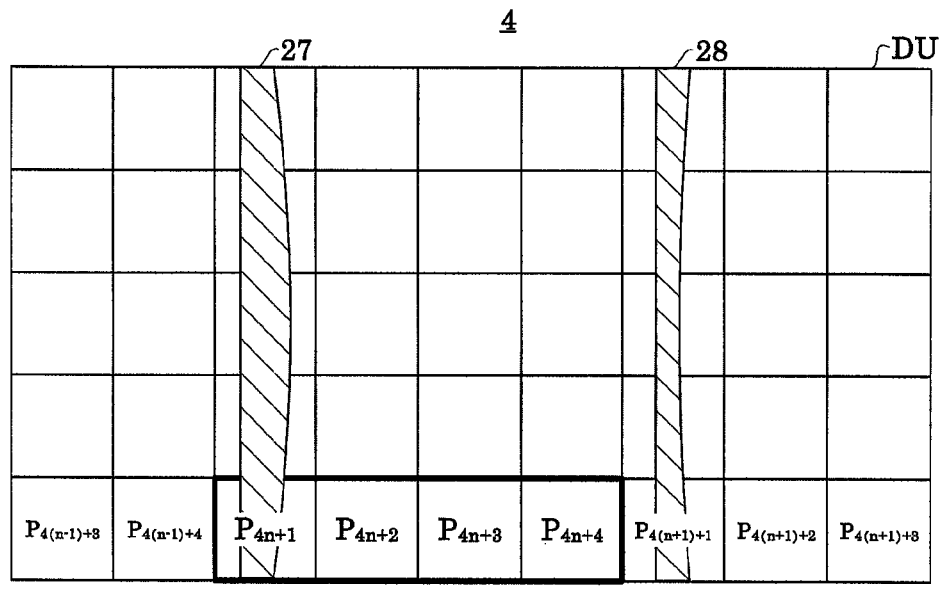
FIG. 11 is an explanatory view showing pixels of the FPD with foil shadows according to the embodiments.

The normal correction mode is a correction mode selected when the SID is the reference SID and the movement of the foil shadows due to bending of the C-arm 5 also is negligible. That is, it is a correction mode for a case where the foil shadows do not protrude from the pixels arranged beforehand to have the foil shadows cast thereon. Assuming that, as shown in FIG. 11, the pixels arranged beforehand to have the foil shadows cast thereon are set to $P_{4n+1}$ (where n is an integer 0 or more) in the direction of row, i.e. in the transverse direction, the foil shadows are certainly cast on the pixels affixed with $P_{4n+1}$ at intervals of four pixels. The shape of the grid foil strips 3a is not strictly uniform, and minute shifts will occur with the arrangement of the grid foil strips 3a also. These result in variations in the width of the foil shadows as seen in a foil shadow 27 or foil shadow 28. However, the foil shadows do not fall on the transversely adjoining pixels affixed with $P_{4n+2}$, $P_{4n+3}$ and $P_{4n+4}$ other than the pixels $P_{4n+1}$. So, the foil shadows are corrected using a pixel set extracting the pixels $P_{4n+2}$, $P_{4n+3}$ and $P_{4n+4}$ which are three pixel sets between the foil shadows. This correction method is the normal correction mode.

Figure 12:
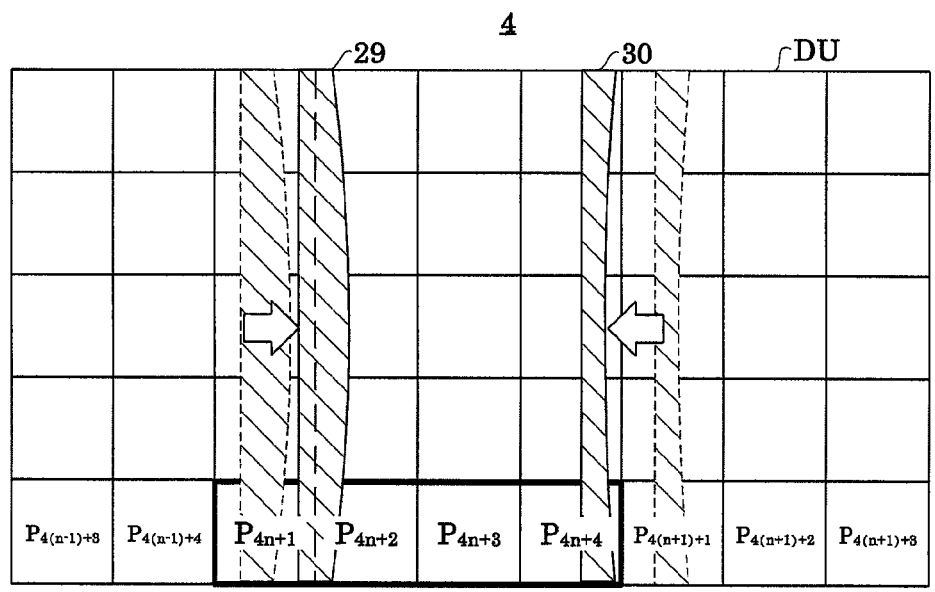
FIG. 12 is an explanatory view showing the pixels of the FPD with foil shadows according to the embodiments.

The special correction mode is a correction method for a case where the SID is moved from the reference SID or the X-ray tube focus is moved by bending of the C-arm 5, and the foil shadows protrude to adjoining pixels from the pixels arranged beforehand to have the foil shadows falling thereon. Assuming that the pixels arranged beforehand to have the foil shadows falling thereon are set to $P_{4n+1}$ (where n is an integer 0 or more) in the transverse direction, the foil shadows are moved from the pixels $P_{4n+1}$ by the SID movement or bending of the C-arm 5 as shown in FIG. 12. For example, a foil shadow 29 falls to straddle the pixels $P_{4n+1}$ and transversely adjoining pixels $P_{4n+2}$. A foil shadow 30 has moved from pixels $P_{4(n+1)+1}$ completely onto pixels $P_{4n+4}$. Thus, those positively free of the foil shadows as a result of the movement of about 40 µm are pixels $P_{4n+3}$ located in the middle between the pixels arranged beforehand to have the foil shadows cast thereon. So, the foil shadows are corrected using a pixel set extracting the pixels $P_{4n+3}$ located in the middle between the pixels arranged beforehand to have the foil shadows cast thereon. This correction method is the special correction mode.

When the correction mode selecting unit 19 has selected the normal correction mode, the first approximate fluoroscopic image calculating unit 20 elects from the X-ray detection image stored in the image memory unit 18 a pixel set extracting the pixels $P_{4n+2}$, $P_{4n+3}$ and $P_{4n+4}$ not influenced by the foil shadows, and calculates a first approximate fluoroscopic image of the patient M. Thus, the election of the pixel set not influenced by the foil shadows elects all the pixels other than the pixels $P_{4n+1}$ arranged beforehand to have the foil shadows cast thereon.

Figure 13A:
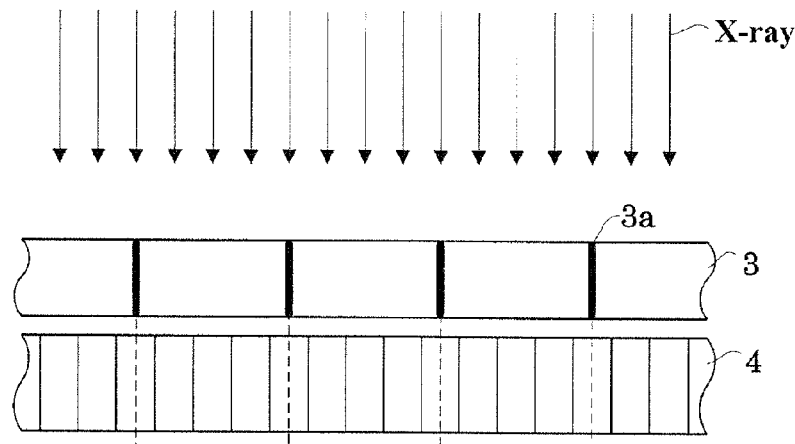
FIGS. 13(*a*) and (*b*) are explanatory views showing detection values of the pixels with foil shadows according to the embodiments.
Figure 13B:
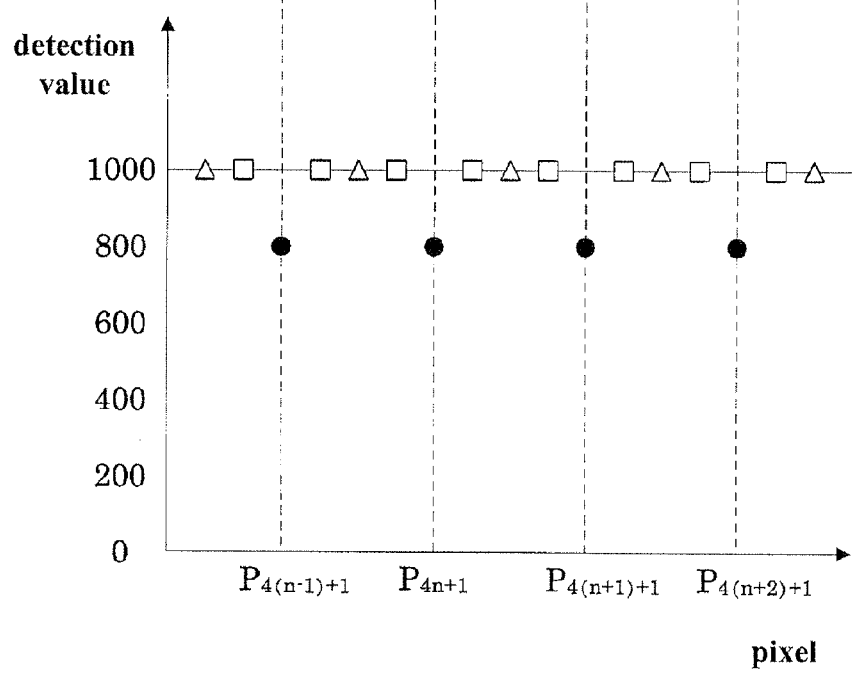

When X-raying is carried out without the patient M placed on the top board 8 as shown in FIG. 13(a), X-ray detection signal values (● mark) of the pixels $P_{4n+1}$ having the foil shadows of the grid foil strips 3a cast thereon, as shown in FIG. 13(b), are values reduced about 20% from X-ray detection signal values (Δ mark and □ mark) of the other pixels.

Figure 14A:
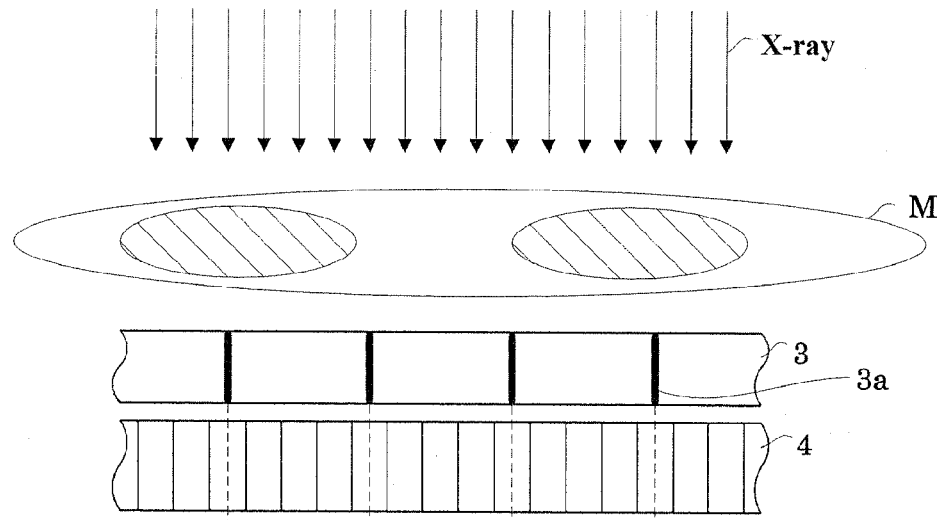
FIGS. 14(*a*) and (*b*) are explanatory views showing detection values of the pixels with foil shadows according to the embodiments.
Figure 14B:
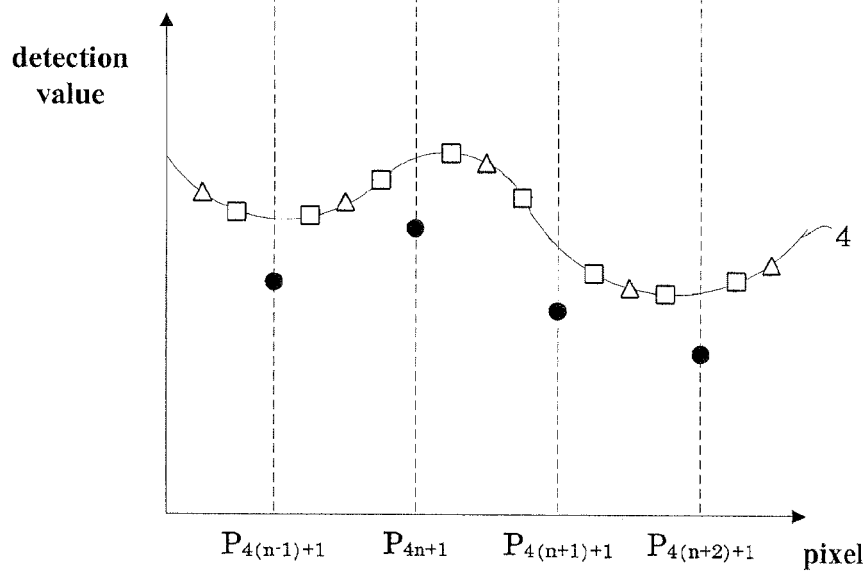

Next, as shown in FIG. 14(a), when X-raying is carried out with the patient M placed on the top board 8, X-ray detection signal values (● mark) of the pixels $P_{4n+1}$ having the foil shadows of the grid foil strips 3a cast thereon, as in the above case, and as shown in FIG. 14(b), are values reduced from X-ray detection signal values (Δ mark and □ mark) of the other pixels. Then, the pixel set extracting the pixels $P_{4n+2}$, $P_{4n+3}$ and $P_{4n+4}$ not influenced by the foil shadows is elected, and the X-ray detection signal values (● mark) of the pixels $P_{4n+1}$ having the foil shadows of the grid foil strips 3a cast thereon are interpolated with these X-ray detection signal values (Δ mark and □ mark) in the pixel set. This interpolating method can estimate a fluoroscopic image of the patient M with high accuracy by quadratic interpolation or cubic interpolation such as cubic spline method. In this way, the first approximate image which is an estimated fluoroscopic image can be calculated. The first approximate image calculated by interpolation includes interpolation errors.

When the correction mode selecting unit 19 has selected the special correction mode, the second approximate fluoroscopic image calculating unit 21 elects a pixel set not influenced by the foil shadows from the X-ray detection image stored in the image memory unit 18, and calculates a second approximate fluoroscopic image of the patient M. In the special correction mode, the foil shadows may have moved also to the pixels $P_{4n+2}$ or $P_{4(n-1)+4}$ adjoining the pixels $P_{4n+1}$ having the foil shadows of the grid foil strips 3a cast thereon. So, the second approximate fluoroscopic image calculating unit 21 elects the pixel set extracting the pixels $P_{4n+3}$ not having the foil shadows even if the foil shadows are moved by movement of the SID or C-arm 5, and with these X-ray detection signal values (Δ mark) of the pixel set, interpolates the X-ray detection signal values (● mark and □ mark) of the pixels $P_{4n+1}$ having the foil shadows of the grid foil strips 3a cast thereon and the pixels $P_{4n+2}$ or $P_{4n+4}$ to which the foil shadows may move. This interpolating method can estimate a fluoroscopic image of the patient M with high accuracy by cubic interpolation such as cubic spline method. In this way, the second approximate image which is an estimated fluoroscopic image can be calculated. The second approximate image calculated by interpolation includes interpolation errors.

The simple term approximate fluoroscopic image will be used when referring to both the first approximate fluoroscopic image and the second approximate fluoroscopic image. The first approximate fluoroscopic image calculating unit and the second approximate fluoroscopic image calculating unit correspond to the approximate fluoroscopic image calculating unit in this invention.

The foil shadow image calculating unit 22 calculates a grid foil shadow image from a difference between the X-ray detection image and the approximate fluoroscopic image. That is, the grid foil shadow image which is an image showing only the foil shadows can be obtained by calculating an image consisting of X-ray detection signals corresponding to decreases made by superimposed foil shadows. Since the foil shadows are formed in the longitudinal direction along the grid foil strips 3a, the grid foil shadow image is also image data having detection values lined up in the longitudinal direction. Since the grid foil shadow image is calculated based on the approximate fluoroscopic image including interpolation errors, the interpolation errors are included also in the grid foil shadow image.

The foil shadow standard image calculating unit 23 calculates a grid foil shadow standard image by averaging in the longitudinal direction the grid foil shadow image having the detection values lined up in the longitudinal direction. That is, as shown in FIGS. 11 and 12, correction is made by averaging variations in the detection value of the foil shadows due to the shape nonuniformity of the foil shadows. For example, an average value of the detection values (pixel values) of the detecting pixels in 30 vertical pixels of the pixels to be corrected is calculated, and the pixel values of the pixels to be corrected are replaced with this average value. The grid foil shadow standard image can be calculated by carrying out this process for all the detecting pixels. The interpolation errors included in the grid foil shadow image can be removed by averaging the grid foil shadow image in the longitudinal direction, i.e. length direction, of the foil shadows.

The subtracting unit 24 calculates a foil shadow removed fluoroscopic image from a difference between the X-ray detection image stored in the image memory unit 18 and the grid foil shadow standard image. By removing standardized foil shadows from the X-ray detection image, a fluoroscopic image of the patient from which the influence of the interpolation errors is removed can be acquired. The subtracting unit 24 corresponds to the foil shadow removed image calculating unit in this invention.

The fluoroscopic image of the patient from which the foil shadows have been removed by the subtracting unit 24 is displayed on the monitor 15 or stored in the storage unit 16 through the main controller 13.

Next, operation of Embodiment 1 in carrying out X-ray fluoroscopy will be described.

First, the radiographer sets an amount of the SID and an amount of movement of the C-arm 5 to the input unit 14. This causes the main controller 13 to transfer the set amount of the SID and amount of movement of the C-arm 5 to the C-arm movement controller 7. The C-arm movement controller 7 causes the C-arm moving mechanism 6 to move the C-arm 5 reflecting each set amount. Next, when a start of X-raying is instructed to the input unit 14, the main controller 13 controls the X-ray tube controller 10 and FPD 4. The X-ray tube controller 10 applies the tube voltage and tube current to the X-ray tube 2 based on instructions from the main controller 13, whereby X-rays are emitted from the X-ray tube 2 to the patient M. X-rays transmitted through the patient M have the scattered X-rays removed by the synchronous grid 3, and fall on the FPD 4 to be detected by the X-ray detecting pixels DU. The X-ray detection signals detected by the X-ray detecting pixels DU are converted from analog to digital by the A/D converter 11. The X-ray detection signals converted to digital are transferred to the image processor 12 to be LOG-transformed by the LOG-transforming unit 17. The LOG-transformed X-ray detection signals are stored as an X-ray detection image in the image memory unit 18.

Figure 15:
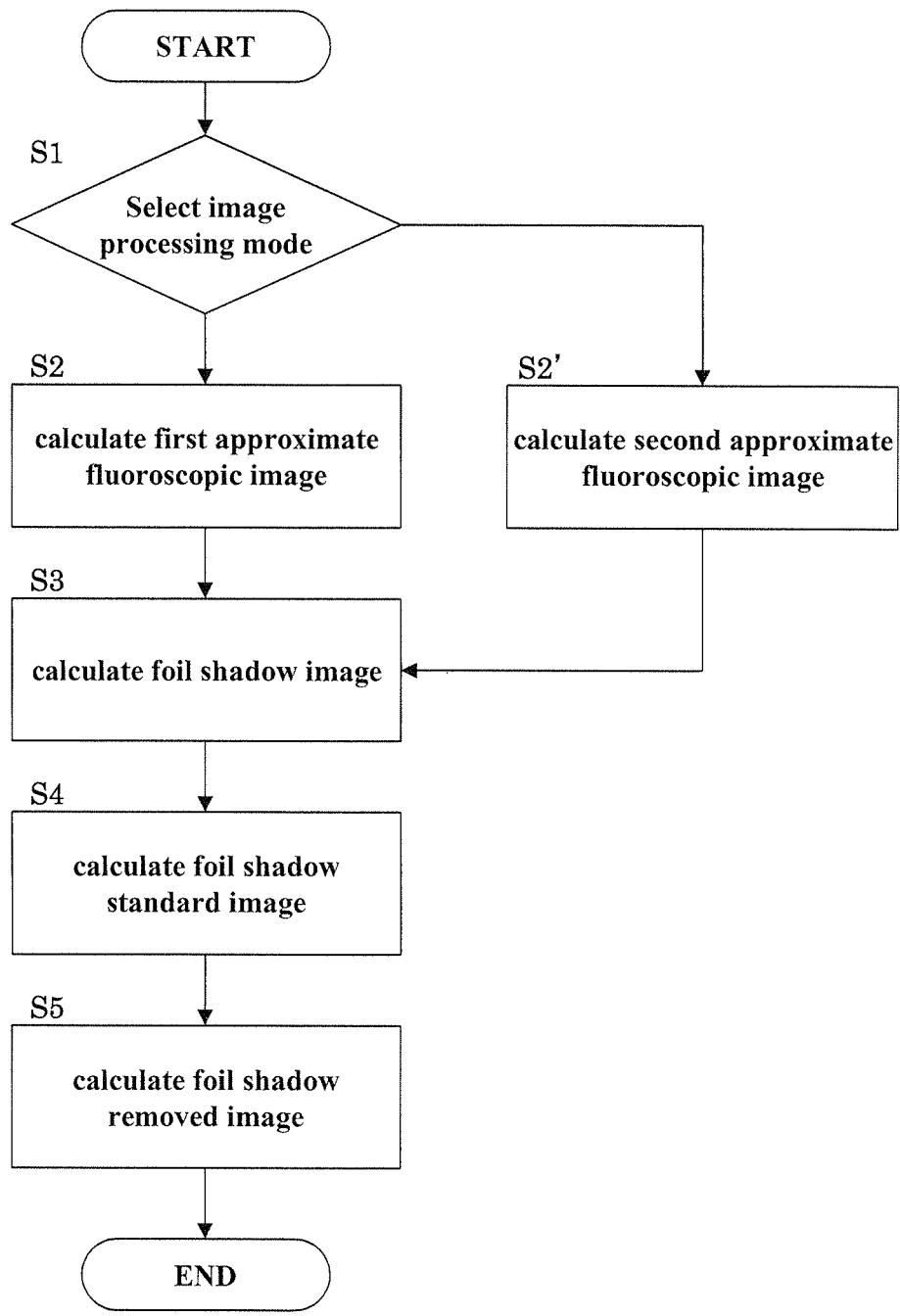
FIG. 15 is a flow chart showing a flow of a foil shadow correction process according to Embodiment 1.

Next, the foil shadows are corrected according to the flow chart shown in FIG. 15. At a time of normal radiography, the foil shadows are corrected in the normal correction mode. The normal radiography means a case where the SID is the reference SID and bending of the C-arm 5 does not influence the foil shadows. The reference SID is 1000 mm in Embodiment 1, but may be set as appropriate. The foil shadows are corrected in the special correction mode when the SID is moved from the reference SID and when bending of the C-arm cannot be disregarded.

Step S1 (Select Correction Mode)

An amount of the SID and an amount of movement of the C-arm 5 set to the input unit 14 by the radiographer are transmitted to the correction mode selecting unit 19 in the image processor 12 through the main controller 13. Based on this information, the correction mode selecting unit 19 selects the normal correction mode or the special correction mode. The normal correction mode is selected when the amount of the SID and the amount of movement of the C-arm 5 do not influence the foil shadows, that is, when the foil shadows do not protrude from the pixels arranged before-hand to have the foil shadows falling thereon. The special correction mode is selected when the amount of the SID and the amount of movement of the C-arm 5 influence the foil shadows, that is, when the foil shadows protrude from the pixels arranged beforehand to have the foil shadows falling thereon.

Step S2 (Calculate First Approximate Fluoroscopic Image)

When the normal correction mode is selected in step S1, the first approximate fluoroscopic image calculating unit 20 elects a pixel set extracting three detecting pixels between the foil shadows, which pixels have no foil shadow falling thereon. Further, from the pixel values of this pixel set, the detection values of the detecting pixels not elected are interpolated, and a first approximate fluoroscopic image seeing through the patient M is calculated.

Step S2 (Calculate Second Approximate Fluoroscopic Image)

When the special correction mode is selected in step S1, the second approximate fluoroscopic image calculating unit 21 elects a pixel set extracting detecting pixels in the middle between the foil shadows, which pixels have no foil shadows falling thereon. Further, from the pixel values of this pixel set, the detection values of the detecting pixels not elected are interpolated, and a second approximate fluoroscopic image seeing through the patient M is calculated.

Step S3 (Calculate Foil Shadow Image)

The foil shadow image calculating unit 22 calculates a grid foil shadow image from a difference between the X-ray detection image stored in the image memory unit 18 and the approximate fluoroscopic image calculated by the first approximate fluoroscopic image calculating unit 20 or second approximate fluoroscopic image calculating unit 21. That is, the grid foil shadow image can be obtained since an image consisting only of the X-ray detection signals from the detecting pixels shadowed by the foil shadows is calculated.

Step S4 (Calculate Foil Shadow Standard Image)

The foil shadow standard image calculating unit 23 calculates a grid foil shadow standard image by averaging in the longitudinal direction the grid foil shadow image having the detection values lined up in the longitudinal direction. Since each grid foil strip 3a is pulled and held in the longitudinal direction, i.e. in the direction of the foil strips, relatively small variations occur to the foil shadows in the longitudinal direction of the grid foil strips 3a. Amplifier noise and quantum noise can be corrected by averaging the foil shadows. For example, an average value of the detection values of several tens of vertical pixels of the pixels to be corrected is calculated, and the pixel values of the pixels to be corrected are replaced with this average value. The grid foil shadow standard image is calculated by carrying out this process for all the detecting pixels.

Step S5 (Calculate Foil Shadow Removed Image)

The subtracting unit 24 calculates a foil shadow removed fluoroscopic image from a difference between the X-ray detection image and the grid foil shadow standard image. Consequently, a fluoroscopic image of the patient from which the foil shadows are removed can be acquired. The fluoroscopic image of the patient from which the foil shadows have been removed by the subtracting unit 24 is displayed on the monitor 15 or stored in the storage unit 16 through the main controller 13.

Thus, according to the X-ray fluoroscopic apparatus 1 in Embodiment 1, by averaging in the longitudinal direction the foil shadow image projected to the X-ray detecting pixels DU, interpolation errors included when calculating the approximate fluoroscopic image can be removed, and further an accurate foil shadow image with amplifier noise and quantum noise removed therefrom can be obtained. Consequently, the foil shadows of the synchronous grid can be removed from the fluoroscopic image, without artifacts appearing thereon.

Further, even when the foil shadows move from the X-ray detecting pixels DU arranged beforehand to have the foil shadows falling thereon to adjoining detecting pixels, such as when the SID and C-arm 5 are moved, the foil shadows can be removed with high accuracy since a foil shadow image is obtained by approximating the fluoroscopic image by interpolation from a pixel set extracting pixels which are with certainty free from the foil shadows. Thus, the foil shadows can be removed fully also when a minute uncontrollable movement of the X-ray tube focus takes place. Consequently, when the foil shadows do not move across the pixels, and also when they do, the interpolation process can be performed appropriately, and further an image with an excellent signal-noise ratio can be acquired due to an advantage of the synchronous grid with a direct X-ray sensitivity about 20% higher than that of the conventional type grid.

The synchronous grid 3 and the radiation detector (FPD 4) are arranged beforehand so that the foil shadows may fall on every four pixels. Even if the foil shadows move, the movement of the foil shadows is contained within the adjoining pixels at opposite sides of the pixels arranged beforehand to have the grid foils projected thereon. It is therefore possible to provide pixels which certainly have no foil shadows falling thereon.

Embodiment 2

Figure 16:
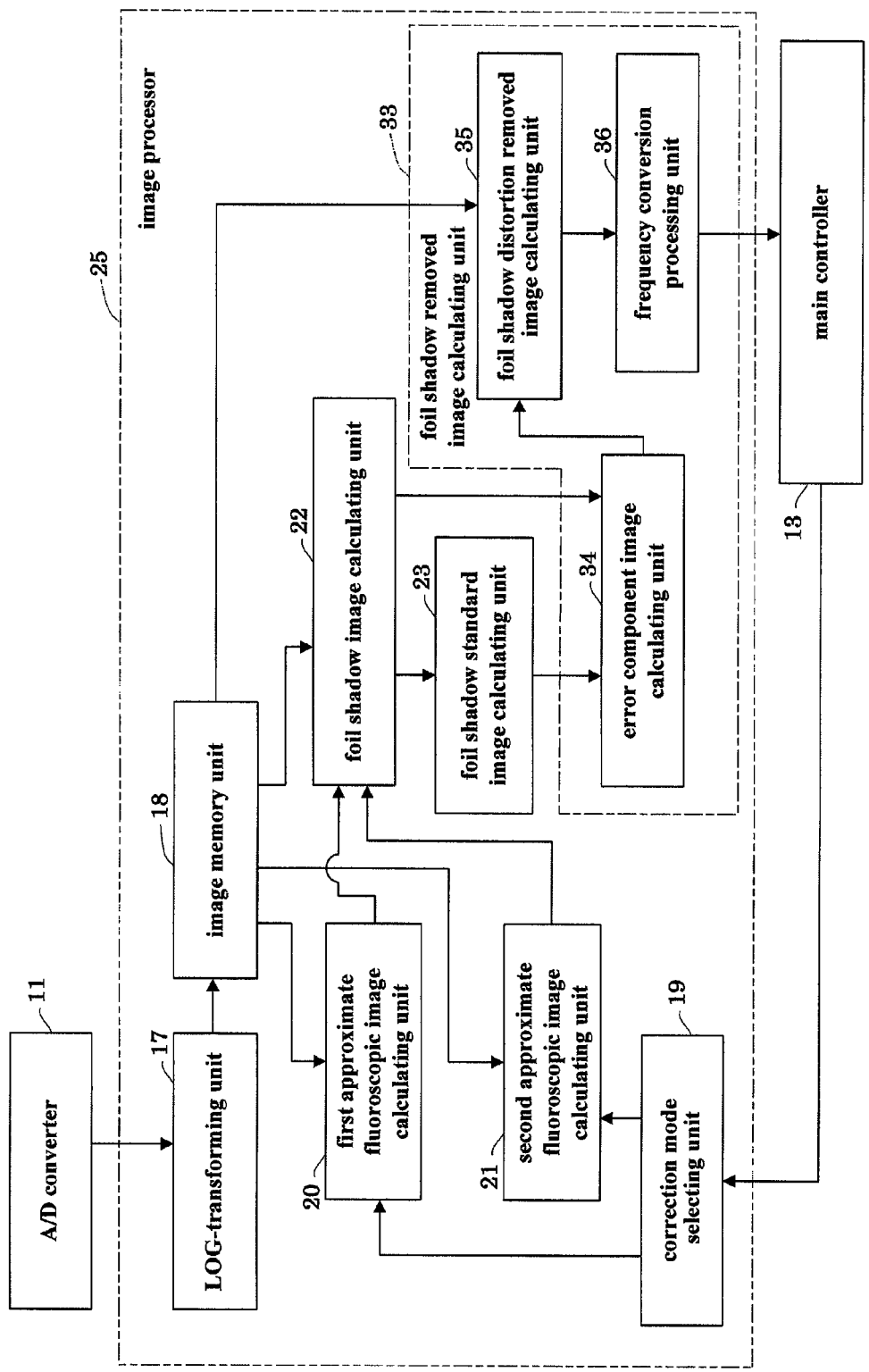
FIG. 16 is a block diagram showing a construction of an image processor according to Embodiment 2.
Figure 17:
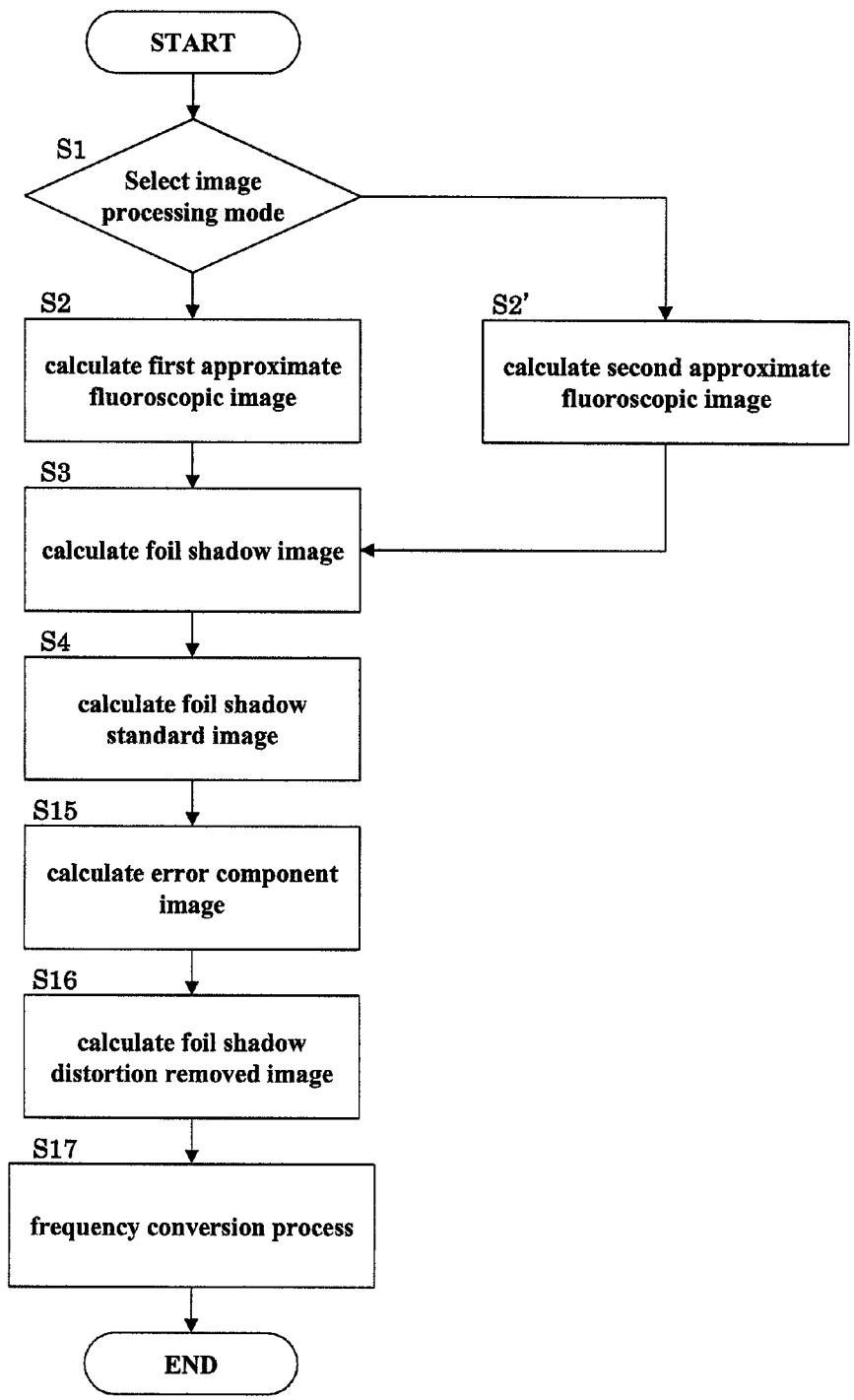
FIG. 17 is a flow chart showing a flow of a foil shadow correction process according to Embodiment 2.

Next, Embodiment 2 of this invention will be described with reference to FIGS. 16 and 17. FIG. 16 is a block diagram showing a construction of an image processor according to Embodiment 2. FIG. 17 is a flow chart showing a flow of a foil shadow correction process according to Embodiment 2. In FIGS. 16 and 17, the parts with the same reference signs as used in Embodiment 1 are the same as in Embodiment 1 and will not be described again. Embodiment 2 has made changes in the subtracting unit of Embodiment 1. Therefore, the aspects of the X-ray fluoroscopic apparatus other than those described here are the same as in Embodiment 1.

The characteristic of Embodiment 2 lies in that the foil shadows are removed by frequency conversion. An image processor 25 includes, in addition to the LOG-transforming unit 17, image memory unit 18, correction mode selecting unit 19, first approximate fluoroscopic image calculating unit 20, second approximate fluoroscopic image calculating unit 21, foil shadow image calculating unit 22 and foil shadow standard image calculating unit 23, a foil shadow removed image calculating unit 33 for obtaining a foil shadow removed image by removing the grid foil shadows from a fluoroscopic image based on the grid foil shadow standard image.

The foil shadow removed image calculating unit 33 has an error component image calculating unit 34 for calculating an error component image from a difference between the grid foil shadow image and the grid foil shadow standard image, a foil shadow distortion removed image calculating unit 35 for calculating a foil shadow distortion removed image in which distortions of the foil shadows are removed, from a difference between the X-ray detection image stored in the image memory unit 18 and the error component image, and a frequency conversion processing unit 36 for calculating a foil shadow removed X-ray detection image by performing a frequency conversion process on the foil shadow distortion removed image.

The error component image calculating unit 34 calculates an error component image from the difference between the grid foil shadow image and the grid foil shadow standard image. That is, using an ideal foil shadow image in the grid foil shadow image as a criterion, variations of the foil shadow due to the shape nonuniformity of every grid foil strip 3a can be calculated.

The foil shadow distortion removed image calculating unit 35 calculates a foil shadow distortion removed image in which distortions of the foil shadows are removed, from the difference between the X-ray detection image stored in the image memory unit 18 and the error component image. The variations in the detection values of the foil shadows due to the shape distortion of every grid foil strip 3a are thereby corrected. That is, it can be said that all the foil shadows in the foil shadow distortion removed image are ideal shadows of the grid foil strips, and that the sizes of the foil shadows are also uniform.

The frequency conversion processing unit 36 calculates a foil shadow removed fluoroscopic image by performing a frequency conversion process on the foil shadow distortion removed image. Since the foil shadow distortion removed image is an image where foil shadows with the variations corrected are superimposed on a fluoroscopic image of the patient, the foil shadows can be removed by performing the frequency conversion process. Consequently, a fluoroscopic image of the patient with the foil shadows removed therefrom can be acquired.

The fluoroscopic image of the patient from which the foil shadows have been removed by the frequency conversion processing unit 36 is displayed on the monitor 15 or stored in the storage unit 16 through the main controller 13.

Next, operation of Embodiment 2 in carrying out X-ray fluoroscopy will be described. Step S01 to step S04 are the same as in Embodiment 1, and will not be described again.

Step S15 (Calculate Error Component Image)

The error component image calculating unit 34 calculates an error component image from the difference between the grid foil shadow image and the grid foil shadow standard image. That is, variations of the foil shadow of every grid foil strip 3a are calculated using the ideal foil shadow image in the grid foil shadow image as a criterion.

Step S16 (Calculate Foil Shadow Distortion Removed Image)

The foil shadow distortion removed image calculating unit 35 calculates a foil shadow distortion removed image in which distortions of the foil shadows are removed, from the difference between the X-ray detection image stored in the image memory unit 18 and the error component image. The variations in the detection values of the foil shadows due to distortions of the grid foil strips 3a are thereby corrected.

Step S17 (Frequency Conversion Process)

The frequency conversion processing unit 36 calculates a foil shadow removed fluoroscopic image by performing a frequency conversion process on the foil shadow distortion removed image. Since the foil shadow distortion removed image is an image where uniform foil shadows with the variations corrected are superimposed on a fluoroscopic image of the patient, the foil shadows can be removed by performing the frequency conversion process. Consequently, a fluoroscopic image of the patient with the foil shadows removed therefrom can be acquired.

Thus, according to the X-ray fluoroscopic apparatus 1 in Embodiment 2, by averaging in the longitudinal direction the foil shadow image projected to the X-ray detecting pixels DU, an accurate foil shadow image with amplifier noise and quantum noise removed therefrom can be obtained. Further, since the foil shadow distortion removed image calculating unit 35 subtracts from a fluoroscopic image the error component image which is a difference between the foil shadow image and the averaged foil shadow standard image, the foil shadows of all the grid foil strips 3a become uniform, and the foil shadows can be removed by frequency conversion. Consequently, the foil shadows of the synchronous grid can be removed, without artifacts appearing thereon.

Embodiment 3

Figure 18:
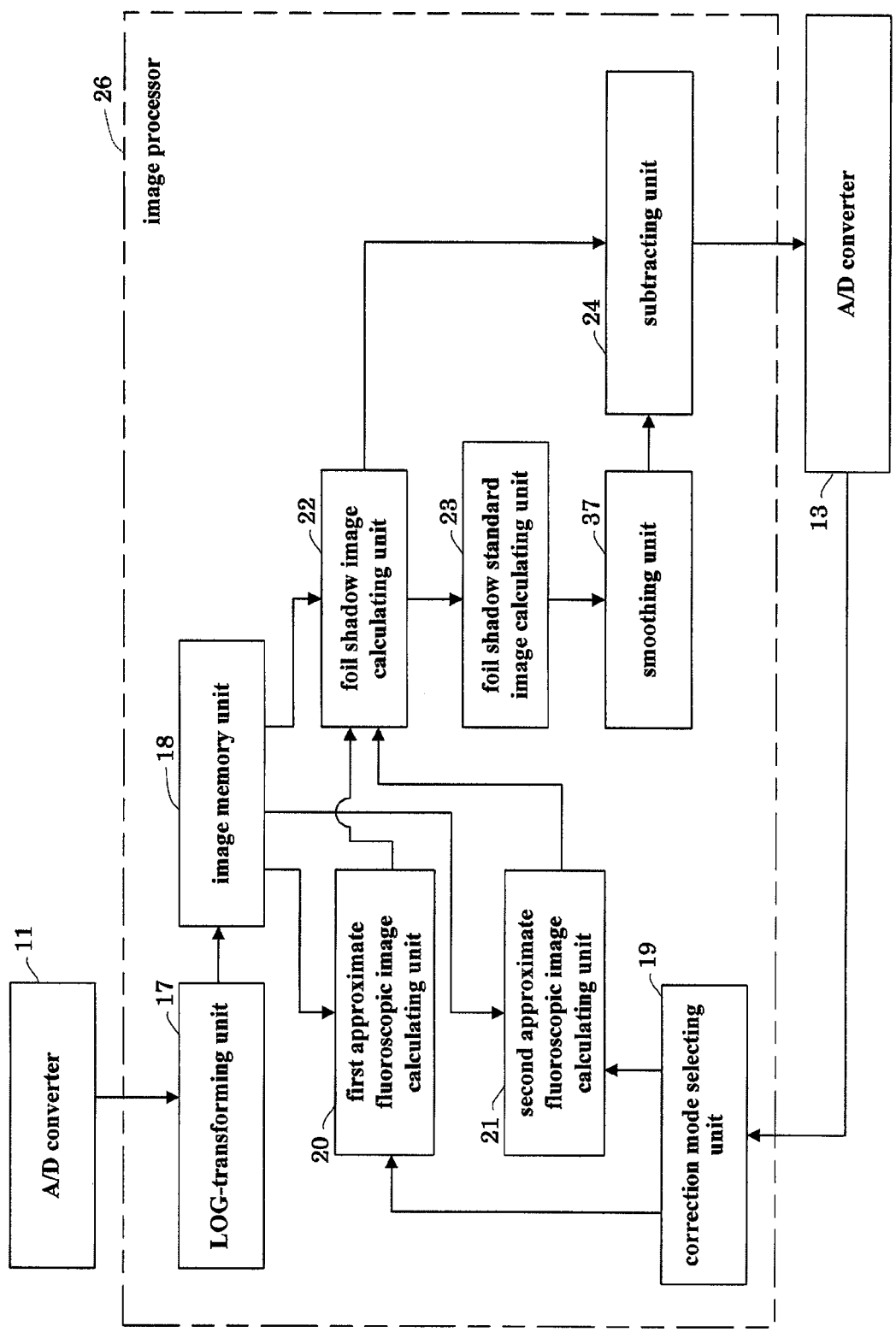
FIG. 18 is a block diagram showing a construction of an image processor according to Embodiment 3.
Figure 20:
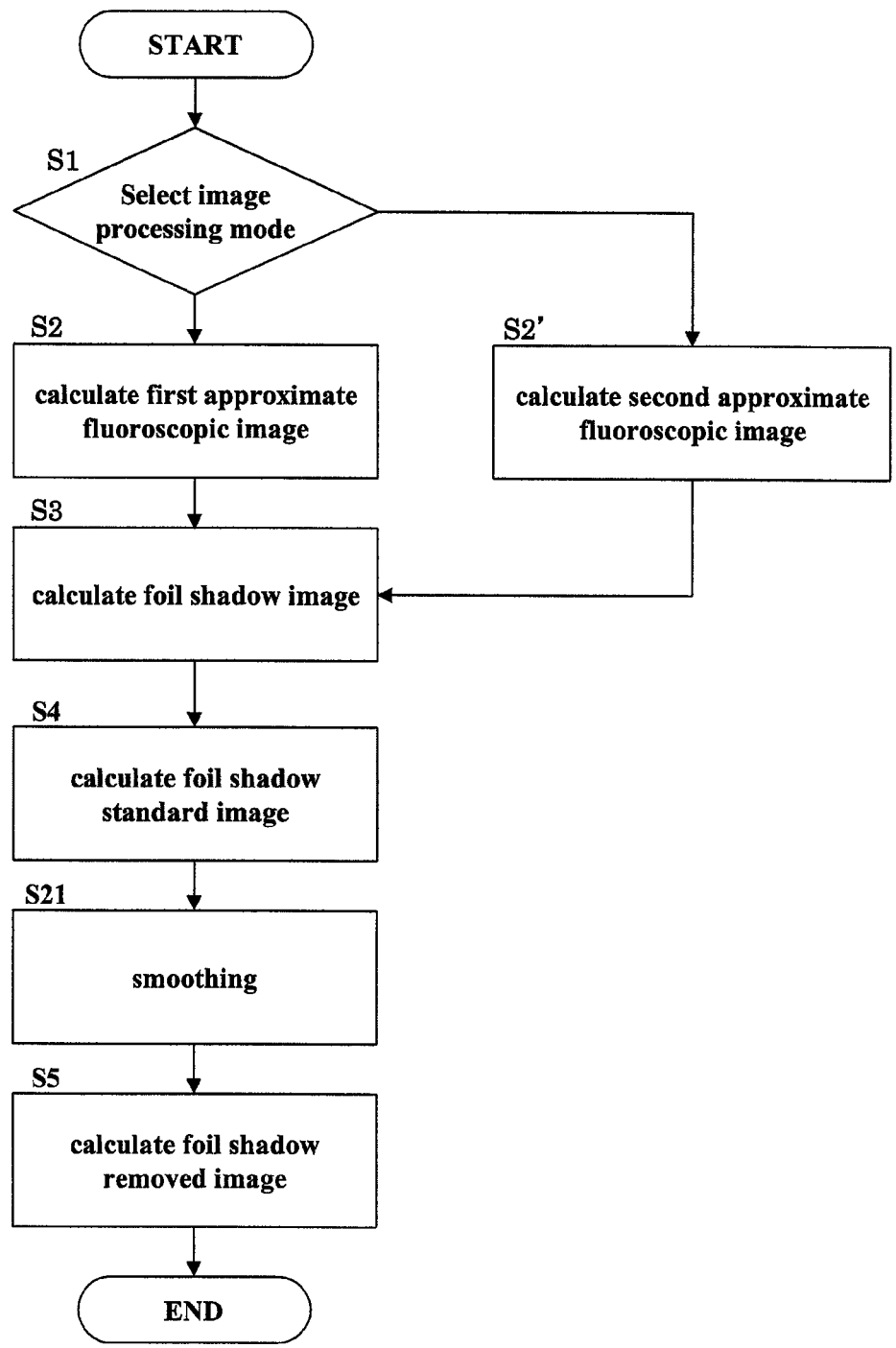
FIG. 20 is a flow chart showing a flow of a foil shadow correction process according to Embodiment 3.

Next, Embodiment 3 of this invention will be described with reference to FIGS. 18, 19 and 20. FIG. 18 is a block diagram showing a construction of an image processor according to Embodiment 3. FIG. 19 an explanatory view showing image processing according to Embodiment 3. FIG. 20 is a flow chart showing a flow of a foil shadow correction process according to Embodiment 3. In FIGS. 18, 19 and 20, the parts with the same reference signs as used in Embodiment 1 are the same as in Embodiment 1, and will not be described again. Embodiment 3 has made changes in the calculation of the grid foil shadow standard image in Embodiment 1. Therefore, the aspects of the X-ray fluoroscopic apparatus other than those described here are the same as in Embodiment 1.

In Embodiment 1 described hereinbefore, the foil shadows are standardized by averaging the pixel values in the longitudinal direction. In addition, the pixel values in the transverse direction which is the direction of row may be extracted at intervals of four pixels, respectively, and each extracted image data may be smoothed. As shown in FIG. 18, for example, from the foil shadow standard image for which averaging has been made in the longitudinal direction by the foil shadow standard image calculating unit 23, a smoothing unit 37 now extracts respective pixels in each row at intervals of four pixels which are the number of pixels corresponding to the length of the regular intervals (Gp) at which the grid foil strips 3a are arranged in the transverse direction. That is, as shown in FIG. 19(a), by extracting pixels at intervals of four pixels in each row, row data picking up the pixel value of every fourth pixel is prepared.

It will be described more particularly with reference to FIG. 19(b). When the pixel values in an rth row of the foil shadow standard image are Pr,1, Pr,2, Pr,3, . . . , the pixel values in the rth row are extracted at intervals of four pixels, thereby preparing row data divided into four parts, i.e. rth row—A, rth row—B, rth row—C and rth row—D as shown in FIG. 19(c). Image data of each of rth row—A, rth row—B, rth row—C and rth row—D is every fourth pixel value in the image data of the original rth row.

Although the original row data has relatively large variations, the four new row data (rth row—A, rth row—B, rth row—C and rth row—D) have smooth values with little variations. The four row data with intermittent pixel values of every four pixels are smoothed. By replacing the original foil shadow standard image data with the smoothed four row data (rth row—A, rth row—B, rth row—C and rth row—D), amplifier noise and quantum noise can be removed from the fluoroscopic image which would otherwise be unable to be smoothed in the transverse direction. With this processing step, as shown in FIG. 20, a smoothing step of Step S21 is executed after the foil shadow standard image calculating step of Step S4.

The smoothing step prepares four row data by extracting pixel values at intervals of four pixels within regular intervals at which the grid foil strips are arranged for respective rows of the foil shadow standard image, and smoothes each row data. Further, the original foil shadow standard image is replaced with the four smoothed row data. When the pixels in the regular intervals at which the grid foil strips 3a are arranged are set to a number exceeding four pixels, row data for every set number of pixels is prepared and smoothed.

Embodiment 4

Figure 21:
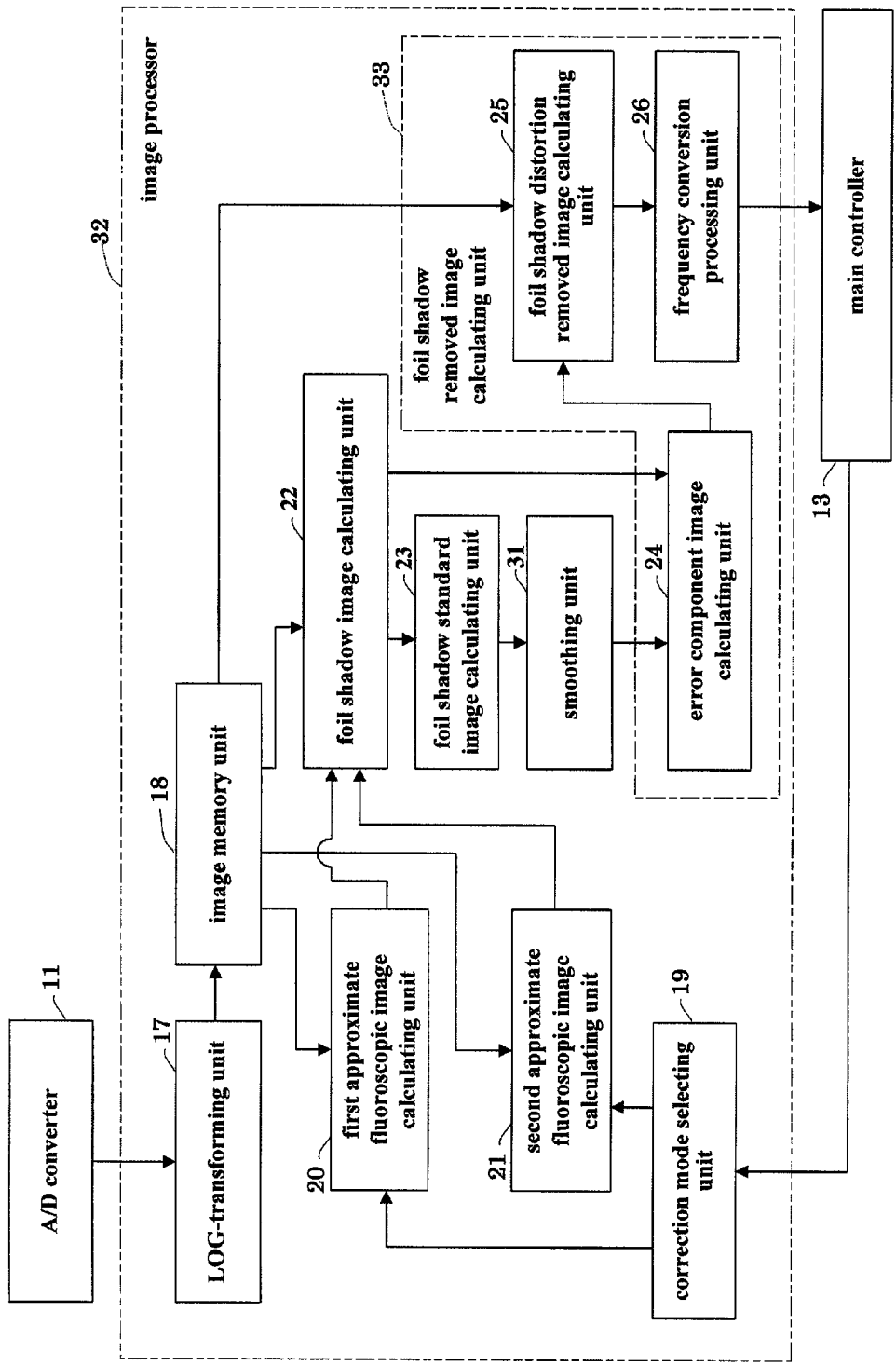
FIG. 21 is a block diagram showing a construction of an image processor according to Embodiment 4.
Figure 22:
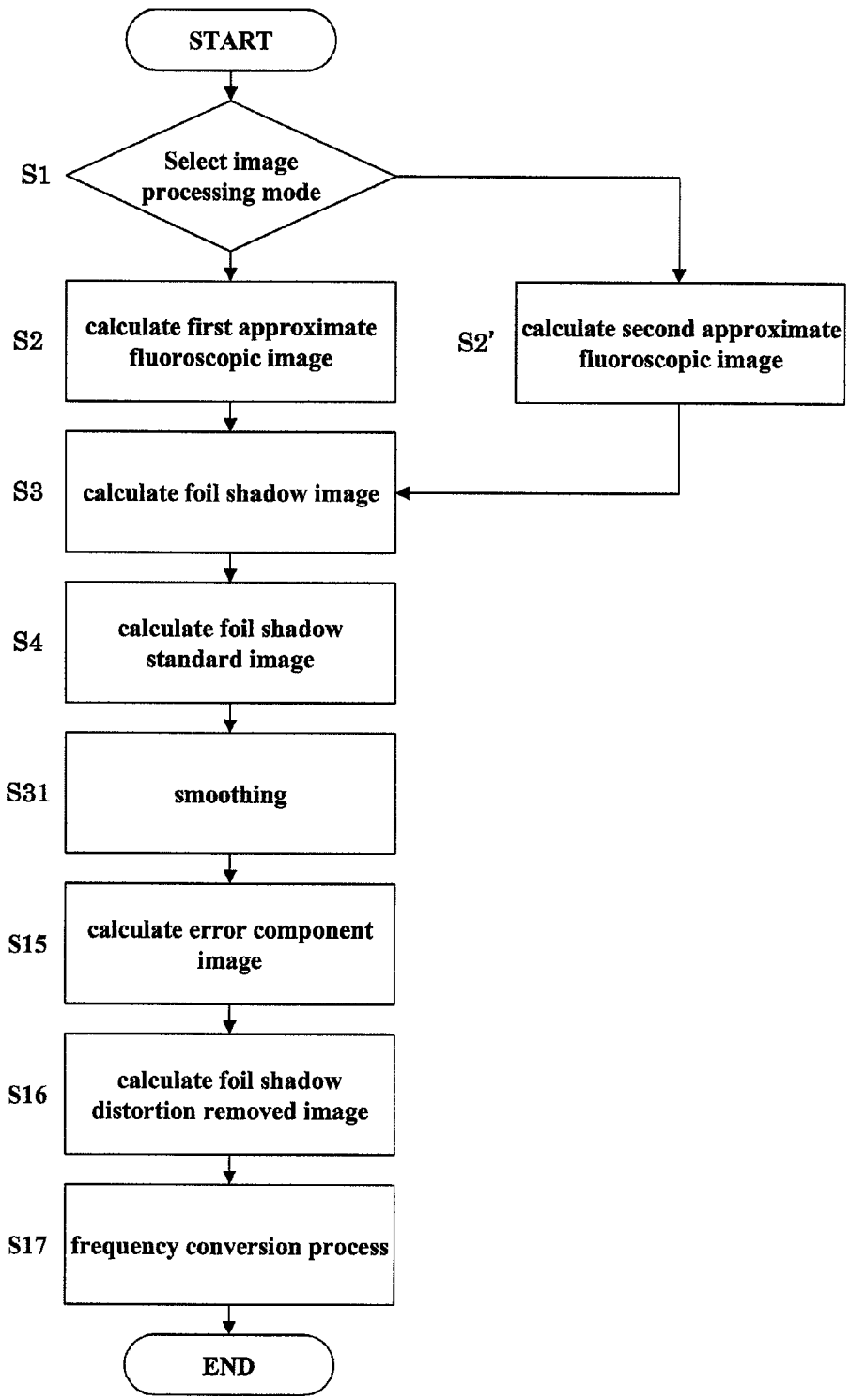
FIG. 22 is a flow chart showing a flow of a foil shadow correction process according to Embodiment 4.
Figure 23:
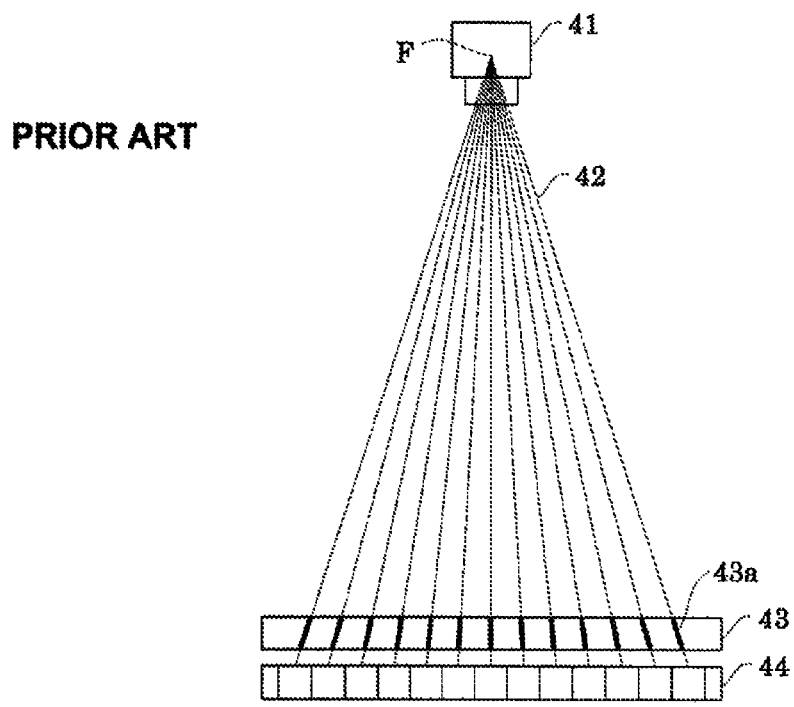
FIG. 23 is a schematic sectional view of a grid of an X-ray fluoroscopic apparatus according to a conventional example.
Figure 24:
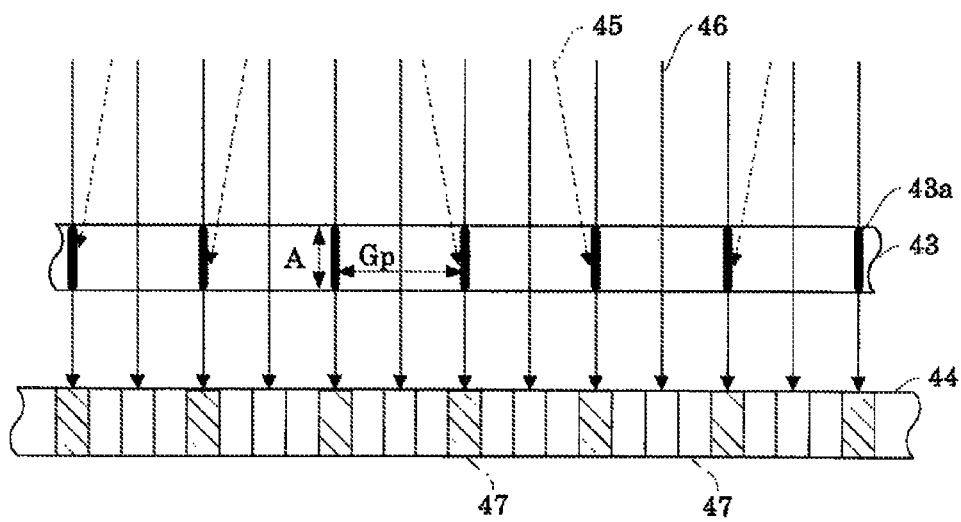
FIG. 24 is a schematic sectional view of the grid of the X-ray fluoroscopic apparatus according to the conventional example.

Next, Embodiment 4 of this invention will be described with reference to FIGS. 21 and 22. FIG. 21 is a block diagram showing a construction of an image processor according to Embodiment 4. FIG. 22 is a flow chart showing a flow of a foil shadow correction process according to Embodiment 4. In FIGS. 21 and 22, the parts with the same reference signs as used in Embodiment 1 to Embodiment 3 are the same as in Embodiment 1 to Embodiment 3 and will not be described again. Embodiment 4 has made changes in the calculation of the grid foil shadow standard image of Embodiment 2. Therefore, the aspects of the X-ray fluoroscopic apparatus other than those described here are the same as in Embodiment 2.

In Embodiment 2 described hereinbefore, the foil shadows are standardized by averaging the pixel values in the longitudinal direction. In addition, the pixel values in the transverse direction which is the direction of row may be extracted at intervals of four pixels, respectively, and each extracted image data may be smoothed. As shown in FIG. 21, for example, from the foil shadow standard image for which averaging has been made in the longitudinal direction by the foil shadow standard image calculating unit 23, a smoothing unit 31 now extracts respective pixels in the transverse direction in each row at intervals of four pixels within the regular intervals at which the grid foil strips 3a are arranged. That is, as shown in FIG. 19, by extracting pixels at intervals of four pixels in each row, row data picking up pixel values of every fourth pixels is prepared.

Although the original row data has relatively large variations, the four new row data have smooth values with little variations. The four row data with intermittent pixel values of every four pixels are smoothed. By replacing the original foil shadow standard image data with the smoothed four row data, amplifier noise and quantum noise can be removed from the fluoroscopic image which would otherwise be unable to be smoothed in the transverse direction. With this processing step, as shown in FIG. 22, a smoothing step of Step S31 is executed out after the foil shadow standard image calculating step of Step S4.

The smoothing step prepares four row data by extracting pixel values at intervals of four pixels within regular intervals at which the grid foil strips are arranged for respective rows of the foil shadow standard image, and smoothes each row data. Further, the original foil shadow standard image is replaced with the four smoothed row data. When the pixels in the regular intervals at which the grid foil strips 3a are arranged are set to a number exceeding four pixels, row data for every set number of pixels is prepared and smoothed.

This invention is not limited to the foregoing embodiments, but may be modified as follows:

(1) In the foregoing embodiments, one grid foil strip 3a is arranged for four pixels, but this is not limitative. In the embodiments, based on the four pixels, one pixel is set to have the foil shadow falling thereon, two pixels are those to which the foil shadow may move, and one pixel is subject to no movement of the foil shadow. Instead of being limited to this, based on eight pixels, two pixels may be set to have the foil shadow falling thereon, four pixels those to which the foil shadow may move, and two pixels subject to no movement of the foil shadow. This can further finely divide the mode of correcting the foil shadows according to the amount of movement of the SID or the amount of movement of the C-arm 5, thereby to improve approximation accuracy of the approximate fluoroscopic image. The basic pixels are not limited to four pixels or eight pixels, but may be any number not less than four. It will serve the purpose if at least four pixels are provided and between grid foil strips 3a there exist(s) a pixel or pixels not influenced by movement of a foil shadow.

(2) In the foregoing embodiments, the detected digital X-ray detection signals are LOG-transformed. However, when the arithmetic process has a margin, the calculation may be carried out without LOG transformation.

(3) In the foregoing embodiments, the correction mode selecting unit 19 automatically selects the first approximate image calculation or second approximated image calculation from an amount of the SID and an amount of movement of the C-arm 5 set and inputted to the input unit 14. Instead, a construction for the operator to select which correction mode at the input unit 14 may be used. The selection of the correction modes may be omitted, such that the second approximate image is always calculated and used. As a method of selecting the correction modes from an amount of the SID and an amount of movement of the C-arm 5, the values of both may be changed beforehand to carry out radiography without the patient M placed on the top board 8, and determine a correction mode to be selected from a pattern of the foil shadows.

(4) In the foregoing embodiments, the pixels not influenced by the foil shadows are extracted with reference to the arrangement of the pixels arranged beforehand to have the foil shadows cast thereon. Instead, pixels actually having the foil shadows cast thereon may be detected by image processing, to extract the other pixels not influenced by the foil shadows. By detecting pixels having the foil shadows cast thereon by image processing in this way, switching may be made based on its result between the normal correction mode and the special correction mode. The special correction mode may employ a pixel set extracting pixels next but one to the pixels having the middles of the foil shadows falling thereon.

The invention claimed is:

1. A grid foil shadow removing method for a radiographic apparatus having a synchronous grid with grid foil strips arranged at regular intervals so that grid foil shadows fall on middles of pixels which detect radiation, the grid foil shadow removing method comprising:

an approximate fluoroscopic image calculating step for obtaining an approximate fluoroscopic image by extracting detection signal values of pixels free from influences of the grid foil shadows from a fluoroscopic image and carrying out an interpolation process thereon;

a grid foil shadow image calculating step for obtaining a grid foil shadow image by determining a difference between the fluoroscopic image and the approximate fluoroscopic image;

a foil shadow standard image calculating step for obtaining a foil shadow standard image by averaging the grid foil shadow image in a longitudinal direction of the grid foil shadows; and a foil shadow removing step for removing the grid foil shadows from the fluoroscopic image based on the foil shadow standard image.

2. The grid foil shadow removing method according to claim 1, wherein the foil shadow removing step removes the grid foil shadows from the fluoroscopic image by a difference between the fluoroscopic image and the foil shadow standard image.

3. The grid foil shadow removing method according to claim 2, comprising a smoothing step for preparing divided row data by extracting, on a row-by-row basis, respective numbers of pixels within the regular intervals at which the grid foil strips are arranged, from the foil shadow standard image averaged in the foil shadow standard image calculating step, and smoothing the row data and replacing the original foil shadow standard image therewith;

wherein the foil shadow removing step removes the grid foil shadows from the fluoroscopic image by a difference between the fluoroscopic image and the foil shadow standard image smoothed.

4. The grid foil shadow removing method according to claim 1, wherein the foil shadow removing step includes:

an error component image calculating step for obtaining an error component image from a difference between the grid foil shadow image and the foil shadow standard image;

a foil shadow distortion removed image calculating step for obtaining a foil shadow distortion removed image by determining a difference between the fluoroscopic image and the error component image; and a frequency conversion processing step for carrying out a frequency conversion process on the foil shadow distortion removed image to remove the grid foil shadows.

5. The grid foil shadow removing method according to claim 4, comprising a smoothing step for preparing divided row data by extracting, on a row-by-row basis, respective numbers of pixels within the regular intervals at which the grid foil strips are arranged, from the foil shadow standard image averaged in the foil shadow standard image calculating step, and smoothing the row data and replacing the original foil shadow standard image therewith;

wherein the error component image calculating step obtains the error component image by determining a difference between the grid foil shadow image and the foil shadow standard image smoothed.

6. The grid foil shadow removing method according to claim 1, comprising an image processing mode selecting step for selecting, based on an amount of an SID and an amount of movement of a C-arm inputted and set, one of a normal correction mode for not correcting movement of the foil shadows between the pixels, and a special correction mode for correcting movement of the foil shadows between the pixels;

wherein, when the normal correction mode is selected in the image processing mode selecting step, the approximate fluoroscopic image calculating step extracts the detection signal values of all pixels other than the pixels arranged beforehand to have the grid foil shadows falling thereon, and carries out an interpolation process thereon; and when the special correction mode is selected in the image processing mode selecting step, the approximate fluoroscopic image calculating step extracts the detection signal values of pixels located in middles between the grid foil strips and free from the foil shadows even if the foil shadows move, and carries out an interpolation process thereon.

7. A radiographic apparatus comprising:

a radiation emitting device for emitting radiation to a patient;

a radiation detecting device having pixels arranged in a two-dimensional array for detecting the radiation transmitted through the patient;

a synchronous grid arranged at regular intervals so that grid foil shadows fall on middles of the pixels;

an approximate fluoroscopic image calculating unit for calculating an approximate fluoroscopic image by extracting a pixel set free from influences of the grid foil shadows from a fluoroscopic image transmitted through the patient and detected and carrying out an interpolation process thereon;

a grid foil shadow image calculating unit for obtaining a grid foil shadow image by determining a difference between the fluoroscopic image and the approximate fluoroscopic image;

a foil shadow standard image calculating unit for obtaining a grid foil shadow standard image by averaging the grid foil shadow image in a longitudinal direction of the grid foil shadows; and a foil shadow removed image calculating unit for obtaining a foil shadow removed image by removing the grid foil shadows from the fluoroscopic image based on the grid foil shadow standard image.

8. The radiographic apparatus according to claim 7, wherein the foil shadow removed image calculating unit obtains the foil shadow removed image by a difference between the fluoroscopic image and the grid foil shadow standard image.

9. The radiographic apparatus according to claim 7, wherein the foil shadow removed image calculating unit includes:

an error component image calculating unit for obtaining an error component image by determining a difference between the grid foil shadow image and the grid foil shadow standard image;

a foil shadow distortion removed image calculating unit for obtaining a foil shadow distortion removed image by determining a difference between the fluoroscopic image and the error component image; and a frequency conversion processing unit for carrying out a frequency conversion process on the foil shadow distortion removed image to remove the grid foil shadows.

10. The radiographic apparatus according to claim 7, comprising:

an input unit for inputting and setting an amount of an SID and an amount of movement of a C-arm; and an correction mode selecting unit for selecting, based on the amount of the SID and the amount of movement of the C-arm inputted and set, a correction mode from a normal correction mode and a special correction mode;

wherein, the approximate fluoroscopic image calculating unit, when the normal correction mode is selected as the correction mode, extracts the detection signal values of all pixels other than the pixels arranged beforehand to have the grid foil shadows falling thereon and carries out an interpolation process thereon, and when the special correction mode is selected as the correction mode, extracts the detection signal values of pixels located in middles between the grid foil strips which are free from the foil shadows even if the foil shadows move and carries out an interpolation process thereon.

11. The radiographic apparatus according to claim 7, comprising a smoothing unit for preparing divided row data by extracting, on a row-by-row basis, respective numbers of pixels within the regular intervals at which the grid foil strips are arranged, from the foil shadow standard image calculated by the foil shadow standard image calculating unit, and smoothing the row data and replacing the original foil shadow standard image therewith.

12. The radiographic apparatus according to claim 7, wherein the synchronous grid and the radiation detecting device are arranged beforehand so that the grid foil shadows fall on every four pixels.

* * * * *